US012718953B2

(12) United States Patent
Kumar et al.

(10) Patent No.: US 12,718,953 B2
(45) Date of Patent: Aug. 25, 2026

(54) POLYGENIC RISK SCORE FOR IN VITRO FERTILIZATION

(71) Applicant: MYOME, INC., Menlo Park, CA (US)

(72) Inventors: Akash Kumar, Palo Alto, CA (US); Kate M. Im, Ellicott City, MD (US); Elan Bechor, New York, NY (US); Luisa Galhardo, Overland Park, KS (US); Abhiram Rao, Redwood City, CA (US); Pauline Ng, Singapore (SG); Matthew Rabinowitz, San Francisco, CA (US)

(73) Assignee: MYOME, INC, Menlo Park, CA (US)

( * ) Notice: Subject to any disclaimer, the term of this patent is extended or adjusted under 35 U.S.C. 154(b) by 1184 days.

(21) Appl. No.: 17/765,073

(22) PCT Filed: Sep. 30, 2020

(86) PCT No.: PCT/US2020/053514
§ 371 (c)(1),
(2) Date: Mar. 30, 2022

(87) PCT Pub. No.: WO2021/067417
PCT Pub. Date: Apr. 8, 2021

(65) Prior Publication Data

US 2022/0367063 A1 Nov. 17, 2022

Related U.S. Application Data

(60) Provisional application No. 63/062,044, filed on Aug. 6, 2020, provisional application No. 62/908,374, filed on Sep. 30, 2019.

(51) Int. Cl.

| | |
|---|---|
| ***G16H 50/30*** | (2018.01) |
| ***G16B 20/40*** | (2019.01) |
| ***G16B 30/10*** | (2019.01) |

(52) U.S. Cl.
CPC ............ *G16H 50/30* (2018.01); *G16B 20/40* (2019.02); *G16B 30/10* (2019.02)

(58) Field of Classification Search
CPC ........ G16H 50/30; G16B 20/40; G16B 30/10; G16B 20/00; G16B 30/00; C12Q 1/6869; C12Q 1/6883
See application file for complete search history.

(56) References Cited

U.S. PATENT DOCUMENTS 8,700,338 B2 4/2014 Oliphant et al.
8,706,422 B2 4/2014 Lo et al.
(Continued)

FOREIGN PATENT DOCUMENTS

CN 105385755 A 3/2016
JP 2017184742 A 10/2017
(Continued)

OTHER PUBLICATIONS

Mora-Sánchez A, Aguilar-Salvador DI, Nowak I. Towards a gamete matching platform: using immunogenetics and artificial intelligence to predict recurrent miscarriage. NPJ Digit Med. Mar. 7, 2019;2:12. doi: 10.1038/s41746-019-0089-x. PMID: 31304361; PMCID: PMC6550222. (Year: 2019).*
(Continued)

*Primary Examiner* — Sun M Li
(74) *Attorney, Agent, or Firm* — Greenberg Traurig, LLP

(57) ABSTRACT

Provided are methods for determining a disease risk associated with an embryo that comprise constructing the genome of the embryo based on (i) one or more genetic variants in the embryo, (ii) a paternal haplotype, (iii) a maternal haplotype (iv) a transmission probability of the paternal haplotype, and (v) a transmission probability of the maternal haplotype; assigning a polygenic risk score to the embryo based on the constructed genome of the embryo;
(Continued)

determining the disease risk associated with the embryo based on the polygenic risk score; and determining transmission of disease causing genetic variants and/or haplotypes from the paternal genome and/or maternal genome to the embryo. Also provided are methods of determining a range of disease risk for potential children for a mother and a potential sperm donor. Also provided are methods of determining disease risk in an individual.

17 Claims, 24 Drawing Sheets

(56) References Cited

U.S. PATENT DOCUMENTS

| | | | | |
|---|---|---|---|---|
| 2006/0099610 | A1 | 5/2006 | Salonen et al. | |
| 2007/0250462 | A1* | 10/2007 | Wilson | G01N 33/6893 706/13 |
| 2009/0299645 | A1* | 12/2009 | Colby | G16B 20/10 506/7 |
| 2012/0185176 | A1* | 7/2012 | Rabinowitz | G16B 30/00 702/19 |
| 2014/0154682 | A1* | 6/2014 | Rabinowitz | C12Q 1/6876 702/20 |
| 2015/0261913 | A1* | 9/2015 | Dewey | G16B 30/00 702/19 |
| 2017/0076038 | A1* | 3/2017 | Rabinowitz | G16B 20/10 |
| 2019/0276879 | A1* | 9/2019 | Sparks | C12Q 1/6827 |
| 2019/0345566 | A1* | 11/2019 | Khera | G16H 50/20 |
| 2021/0254136 | A1* | 8/2021 | Edelman | C12Q 1/6869 |
| 2021/0254164 | A1* | 8/2021 | Hamet | G16B 40/00 |

FOREIGN PATENT DOCUMENTS

| | | | | |
|---|---|---|---|---|
| WO | 2011041485 | A1 | 4/2011 | |
| WO | 2014153757 | A1 | 10/2014 | |
| WO | WO 2017/035010 | | 3/2017 | |
| WO | WO-2017035010 | A1 * | 3/2017 | A61P 37/06 |
| WO | WO-2021077163 | A1 * | 4/2021 | G16B 20/20 |

OTHER PUBLICATIONS

Kumar A, Ryan A, Kitzman JO, Wemmer N, Snyder MW, Sigurjonsson S, Lee C, Banjevic M, Zarutskie PW, Lewis AP, Shendure J, Rabinowitz M. Whole genome prediction for preimplantation genetic diagnosis. Genome Med. Apr. 8, 2015;7(1):35. doi: 10.1186/s13073-015-0160-4. PMID: 26019723; PMCID: PMC4445980. (Year: 2015).*

Khera, A.V., Chaffin, M., Aragam, K.G. et al. Genome-wide polygenic scores for common diseases identify individuals with risk equivalent to monogenic mutations. Nat Genet 50, 1219-1224 (2018). (Year: 2018).*

Treff et al., "Utility and First Clinical Application of Screening Embryos for Polygenic Disease Risk Reduction," Frontiers in Endocrinology, Dec. 2019, vol. 10, Article 845, doi: 10.3389/fendo.2019.00845.

Treff et al., "Validation of concurrent preimplantation genetic testing for polygenic and monogenic disorders, structural rearrangements, and whole and segmental chromosome aneuploidy with a single universal platform," European Journal of Medical Genetics, 2019, 62:103647, 9 pp.

International Search Report and Written Opinion issued Feb. 24, 2021, in PCT/US2020/053514.

International Preliminary Report on Patentability and Written Opinion issued Apr. 5, 2022, in PCT/US2020/053514.

Daetwyler, Hans D., et al. "Imputation of missing genotypes from sparse to high density using long-range phasing." Genetics 189.1 (2011): 317-327.

* cited by examiner

| Disease | Age of onset | Severity |
|---|---|---|
| Breast cancer | adulthood | moderate-severe |
| Celiac disease | birth | moderate |
| Psoriasis | childhood | mild-moderate |

Standardized polygenic risk score

Embryo 2

| | Lifetime Risk | Pop. Risk | Risk Ratio | Percentile |
|---|---|---|---|---|
| Coronary Artery Disease | 26.3% | 25.7% | 1.0x | 56.5% |
| Atrial Fibrillation | 12.6% | 19.4% | 0.6x | 3.9% |
| Type 2 Diabetes | 22.8% | 17.1% | 1.3x | 93.6% |
| Breast Cancer | 18.5% | 12.6% | 1.5x | 89.2% |
| Age-Related Macular Degeneration | 4.2% | 6.6% | 0.6x | 4.3% |
| Psoriasis | 9.7% | 3.6% | 2.7x | 97.7% |
| Colorectal Cancer | 4.2% | 3.6% | 1.2x | 76.4% |
| Deep Venous Thrombosis | 3.0% | 3.4% | 0.9x | 23.4% |
| Parkinson's Disease | 3.1% | 3.3% | 0.9x | 37.5% |
| Glaucoma | 1.9% | 1.8% | 1.0x | 57.3% |
| Rheumatoid Arthritis | 1.7% | 1.4% | 1.2x | 70.6% |
| Celiac Disease | 0.6% | 1.0% | 0.6x | 31.9% |
| Vitiligo | 3.0% | 1.0% | 3.0x | 90.4% |
| Ulcerative Colitis | 0.8% | 0.7% | 1.1x | 61.8% |
| Crohn's Disease | 0.5% | 0.7% | 0.8x | 23.7% |
| Lupus | 0.5% | 0.5% | 1.0x | 53.3% |
| Chronic Lymphocytic Leukemia | 1.0% | 0.4% | 2.5x | 91.7% |
| Type 1 Diabetes | 3.1% | 0.4% | 8.0x | 91.9% |
| Schizophrenia | 0.2% | 0.3% | 0.8x | 35.1% |
| Multiple Sclerosis | 0.4% | 0.3% | 1.3x | 88.3% |

Lifetime Risk axis: 0% 10% 20% 30%

◇ – Population Risk ○ – Embryo Risk ⊚ – Conditions with Elevated Risk FH – Family History

FIG. 16A

Embryo (3)

| | Lifetime Risk (0% – 10% – 20% – 30%) | Pop. Risk | Risk Ratio | Percentile |
|---|---|---|---|---|
| Coronary Artery Disease | 26.1% | 25.7% | 1.0x | 54.6% |
| Atrial Fibrillation | 17.3% | 19.4% | 0.9x | 31.1% |
| Type 2 Diabetes | 24.4% | 17.1% | 1.4x | 97.2% |
| Breast Cancer | 16.8% | 12.6% | 1.3x | 82.0% |
| Age-Related Macular Degeneration | 5.8% | 6.6% | 0.9x | 31.2% |
| Psoriasis | 22.7% | 3.6% | 6.3x | 99.9% |
| Colorectal Cancer | 3.8% | 3.6% | 1.1x | 60.3% |
| Deep Venous Thrombosis | 3.1% | 3.4% | 0.9x | 32.3% |
| Parkinson's Disease | 2.7% | 3.3% | 0.8x | 20.3% |
| Glaucoma | 1.5% | 1.8% | 0.8x | 17.9% |
| Rheumatoid Arthritis | 1.6% | 1.4% | 1.1x | 62.6% |
| Celiac Disease | 1.4% | 1.0% | 1.4x | 62.3% |
| Vitiligo | 3.5% | 1.0% | 3.5x | 93.3% |
| Ulcerative Colitis | 0.6% | 0.7% | 0.8x | 32.1% |
| Crohn's Disease | 0.7% | 0.7% | 1.1x | 61.5% |
| Lupus | 0.3% | 0.5% | 0.6x | 16.2% |
| Chronic Lymphocytic Leukemia | 1.1% | 0.4% | 2.8x | 94.4% |
| Type 1 Diabetes | 1.7% | 0.4% | 4.4x | 83.8% |
| Schizophrenia | 0.3% | 0.3% | 0.8x | 37.8% |
| Multiple Sclerosis | 0.4% | 0.3% | 1.5x | 95.4% |

◇ – Population Risk ○ – Embryo Risk ◎ – Conditions with Elevated Risk FH – Family History

FIG. 16B

Embryo (4)

| | Lifetime Risk (0% – 30%) | Pop. Risk | Risk Ratio | Percentile |
|---|---|---|---|---|
| Coronary Artery Disease | 26.4% | 25.7% | 1.0x | 58.2% |
| Atrial Fibrillation | 18.6% | 19.4% | 1.0x | 43.2% |
| Type 2 Diabetes | 19.2% | 17.1% | 1.1x | 72.9% |
| Breast Cancer | 19.5% | 12.6% | 1.5x | 92.1% |
| Age-Related Macular Degeneration | 4.8% | 6.6% | 0.7x | 11.4% |
| Psoriasis | 2.0% | 3.6% | 0.5x | 12.4% |
| Colorectal Cancer | 4.0% | 3.6% | 1.1x | 68.8% |
| Deep Venous Thrombosis | 3.6% | 3.4% | 1.1x | 60.5% |
| Parkinson's Disease | 3.5% | 3.3% | 1.1x | 62.0% |
| Glaucoma | 2.4% | 1.8% | 1.4x | 94.1% |
| Rheumatoid Arthritis | 1.9% | 1.4% | 1.3x | 79.5% |
| Celiac Disease | 0.5% | 1.0% | 0.5x | 22.1% |
| Vitiligo | 2.0% | 1.0% | 2.0x | 79.8% |
| Ulcerative Colitis | 0.2% | 0.7% | 0.3x | 0.5% |
| Crohn's Disease | 0.3% | 0.7% | 0.5x | 2.5% |
| Lupus | 0.6% | 0.5% | 1.2x | 62.5% |
| Chronic Lymphocytic Leukemia | 0.4% | 0.4% | 0.9x | 46.0% |
| Type 1 Diabetes | 0.7% | 0.4% | 1.9x | 66.2% |
| Schizophrenia | 0.4% | 0.3% | 1.5x | 73.5% |
| Multiple Sclerosis | 0.4% | 0.3% | 1.3x | 89.7% |

◇ – Population Risk ○ – Embryo Risk ⊗ – Conditions with Elevated Risk FH – Family History

FIG. 16C

| System | Condition | Population Risk | HG002 | HG003 | HG004 |
|---|---|---|---|---|---|
| Immune | **Psoriasis** | 3.6% | 9.7% lifetime risk<br>2.7x risk ratio | 22.7% lifetime risk<br>6.3x risk ratio | 2.0% lifetime risk<br>0.5x risk ratio |

FIG. 17A

POLYGENIC RISK SCORE FOR IN VITRO FERTILIZATION

CROSS REFERENCE TO RELATED APPLICATIONS

This application claims the benefit of U.S. Provisional Application No. 62/908,374, filed on Sep. 30, 2019, and U.S. Provisional Application No. 63/062,044, filed on Aug. 6, 2020, each of which are incorporated herein by reference in their entirety.

FIELD

Described are methods for determining disease risk.

BACKGROUND

Currently, IVF clinics test for aneuploidies and single gene disorders that are known to run in families. However, 1 in 2 couples has a family history of common diseases which is impacted by a combination of genetic, environmental and lifestyle risk factors. Moreover, currently sperm donor clinics test for propensity to develop a subset of diseases caused by single gene disorders. There is a need in the art to improve the ability to predict inherited disease risk in an individual and in potential future children.

SUMMARY

Provided are methods for determining a disease risk associated with an embryo, the method comprising: performing whole genome sequencing on a biological sample obtained from a paternal subject to identify a genome associated with the paternal subject; performing whole genome sequencing on a biological sample obtained from a maternal subject to identify a genome associated with the maternal subject; phasing the genome associated with the paternal subject to identify a paternal haplotype; phasing the genome associated with the maternal subject to identify a maternal haplotype; performing sparse genotyping on the embryo to identify one or more genetic variants in the embryo; constructing the genome of the embryo based on (i) the one or more genetic variants in the embryo, (ii) the paternal haplotype, (iii) the maternal haplotype (iv) a transmission probability of the paternal haplotype, and (v) a transmission probability of the maternal haplotype; assigning a polygenic risk score to the embryo based on the constructed genome of the embryo; determining the disease risk associated with the embryo based on the polygenic risk score; determining transmission of monogenic disease causing genetic variants and/or haplotypes from the paternal genome and/or maternal genome to the embryo; and determining a combined disease risk associated with the embryo based on the polygenic disease risk and the transmission of monogenic disease causing genetic variants and/or haplotypes from the paternal genome and/or maternal genome to the embryo.

Also provided are methods for outputting a disease risk score associated with an embryo, the method comprising: receiving a first dataset that comprises paternal genome data and maternal genome data; aligning sequence reads to a reference genome and determining genotypes across the genome using the paternal genome data and the maternal genome data; receiving a second dataset that comprises paternal and maternal sparse genome data; phasing the paternal genome data and the maternal genome data to identify paternal haplotypes and maternal haplotypes; receiving a third dataset that comprises sparse genome data for the embryo, paternal transmission probabilities, and maternal transmission probabilities; applying an embryo reconstruction algorithm to (i) the paternal haplotypes and the maternal haplotypes, (ii) sparse genome data for the embryo and (iii) transmission probabilities of each of the paternal haplotype and the maternal haplotype, to determine a constructed genome of the embryo; applying a polygenic model to the constructed genome of the embryo; outputting the disease risk associated with the embryo; determining transmission of disease causing genetic variants and/or haplotypes from the paternal genome and/or maternal genome to the embryo; and outputting the presence or absence of disease causing variants and/or haplotypes in the embryo. Some methods further comprise outputting a combined disease risk associated with the embryo based on the polygenic disease risk and the transmission of monogenic disease causing genetic variants and/or haplotypes from the paternal genome and/or maternal genome to the embryo.

In some aspects, the methods further comprise using grandpaternal genomic data and/or grandmaternal genomic data to determine paternal haplotypes and/or maternal haplotypes. In some aspects, the methods further comprise using population genotype data and/or population allele frequencies to determine the disease risk of an embryo. In some aspects, the methods further comprise using family history of disease and/or other risk factors to predict disease risk In some aspects, the whole genome sequencing is performed using standard, PCR-free, linked read (i.e. synthetic long read), or long read protocols. In some aspects, the sparse genotyping is performed using microarray technology; next generation sequencing technology of an embryo biopsy; or cell culture medium sequencing. In some aspects, the phasing is performed using population-based and/or molecular based methods (e.g. linked reads). In some aspects, the polygenic risk score is determined by summing the effect across sites in a disease model.

In some aspects, the population genotype data comprises allele frequencies and individual genotypes for at least about 300,000 unrelated individuals in the UK Biobank. In some aspects, the population phenotype data comprises both self-reported and clinically reported (e.g. ICD-10 codes) phenotypes for at least about 300,000 unrelated individuals in the UK Biobank. In some aspects, the population genotype data comprises population family history data that comprises self-reported data for at least about 300,000 unrelated individuals in the UK Biobank and information derived from relatives of those individuals in the UK Biobank. In some aspects, the disease risk is further determined by the fraction of genetic information shared by an affected individual.

Also provided are methods for determining disease risk for one or more potential children, the methods comprising: performing whole genome sequencing on (i) a prospective mother and one or more potential sperm donors or (ii) a prospective father and one or more potential egg donors; phasing the genomes of (i) the prospective mother and the one or more potential sperm donor(s) or (ii) the prospective father and the one or more potential egg donors; simulating gametes based on recombination rate estimates; combining the simulated gametes to produce genomes for the one or more potential children; assigning a polygenic risk score; and determining a distribution of disease probabilities based on the polygenic risk score.

Also provided are methods for outputting a probability distribution of disease risk for potential children, the method comprising: receiving a first dataset that comprises a prospective mother's genome data; receiving one or more datasets that comprise genome data from one or more prospective sperm donor(s); simulating gametes using an estimated recombination rate (e.g., derived from the HapMap consortium); using potential combinations of gametes to produce genomes for one or more potential children; estimating a polygenic risk score for the genome of each of the one or more potential children; and outputting a distribution of disease probabilities based on the polygenic risk scores.

Also provided are methods for determining a range of disease risk for potential children for (i) a prospective mother and a potential sperm donor or (ii) a prospective father and a potential egg donor, the method comprising: (a) performing whole genome sequencing on (i) the prospective mother and the one or more potential sperm donor(s) to obtain a maternal genotype and one or more sperm donor genotype(s) or (ii) the prospective father and the one or more potential egg donor(s) to obtain a paternal genotype and one or more egg donor genotype(s); (b) estimating possible genotypes for one or more potential children using (i) the maternal genotype and the potential sperm donor genotype (s) or (ii) the prospective father genotype and the potential egg donor genotype(s); and (c) estimating the lowest possible polygenic risk score of a potential child using the possible genotypes of the potential children; and (d) estimating the highest possible polygenic risk score of a potential child using the possible genotypes of the potential children.

Also provided are methods for outputting range of disease risk for potential children for (i) a prospective mother and potential sperm donor or (ii) a prospective father and a potential egg donor, the method comprising: (a) receiving a first dataset that comprises a prospective mother's genome data or a prospective father's genome data; (b) receiving one or more datasets that comprise genome data from one or more prospective sperm donor(s) or one or more prospective egg donor(s); (c) deriving possible genotypes for a potential child using the genotypes of (i) the prospective mother and potential sperm donor(s) or (ii) the prospective father and the potential egg donor(s); (d) estimating the lowest polygenic risk score of the potential child by choosing the genotype (of those derived in (c)) at each site in the model that minimizes the score; (e) estimating the highest polygenic risk score of the potential child by choosing the genotype (of those derived in (c)) at each site in the model that maximizes the score; and (f) outputting the range of risk of disease using the lowest and highest scores calculated in (d) and (e).

In some aspects the methods use a dense genotyping array for the sperm donor(s) followed by genotype imputation for sites of interest not directly genotyped. In some aspects, the methods use family history of disease and other relevant risk factors to determine disease risk.

In some aspects, the whole genome sequencing is performed using standard, PCR-free, linked read (i.e. synthetic long read), or long read protocols. In some aspects, the phasing is performed using population-based and/or molecular based methods (e.g. linked reads). In some aspects, the polygenic risk score is determined by summing the effect across all sites in the disease model.

In some aspects, the population genotype data comprises allele frequencies and individual genotypes for at least about 300,000 unrelated individuals in the UK Biobank. In some aspects, the population phenotype data comprises both self-reported and clinically reported (e.g. ICD-10 codes) phenotypes for at least about 300,000 unrelated individuals in the UK Biobank. In some aspects, the population family history comprises self-reported data for at least about 300,000 unrelated individuals in the UK Biobank and information derived from relatives of those individuals in the UK Biobank.

BRIEF DESCRIPTION OF DRAWINGS

FIG. 16 shows the lifetime risk of a variety of conditions in several embryos, with FIG. 16A showing the risk for a first embryo (termed "Embry 2"), FIG. 16B showing the risk for a second embryo (termed "Embryo 3"), and FIG. 16C showing the risk for a third embryo (termed "Embryo 4").

FIG. 17A shows the lifetime risk and risk ratio in several embryos as compared to the general population risk.

DETAILED DESCRIPTION

Figure 1:
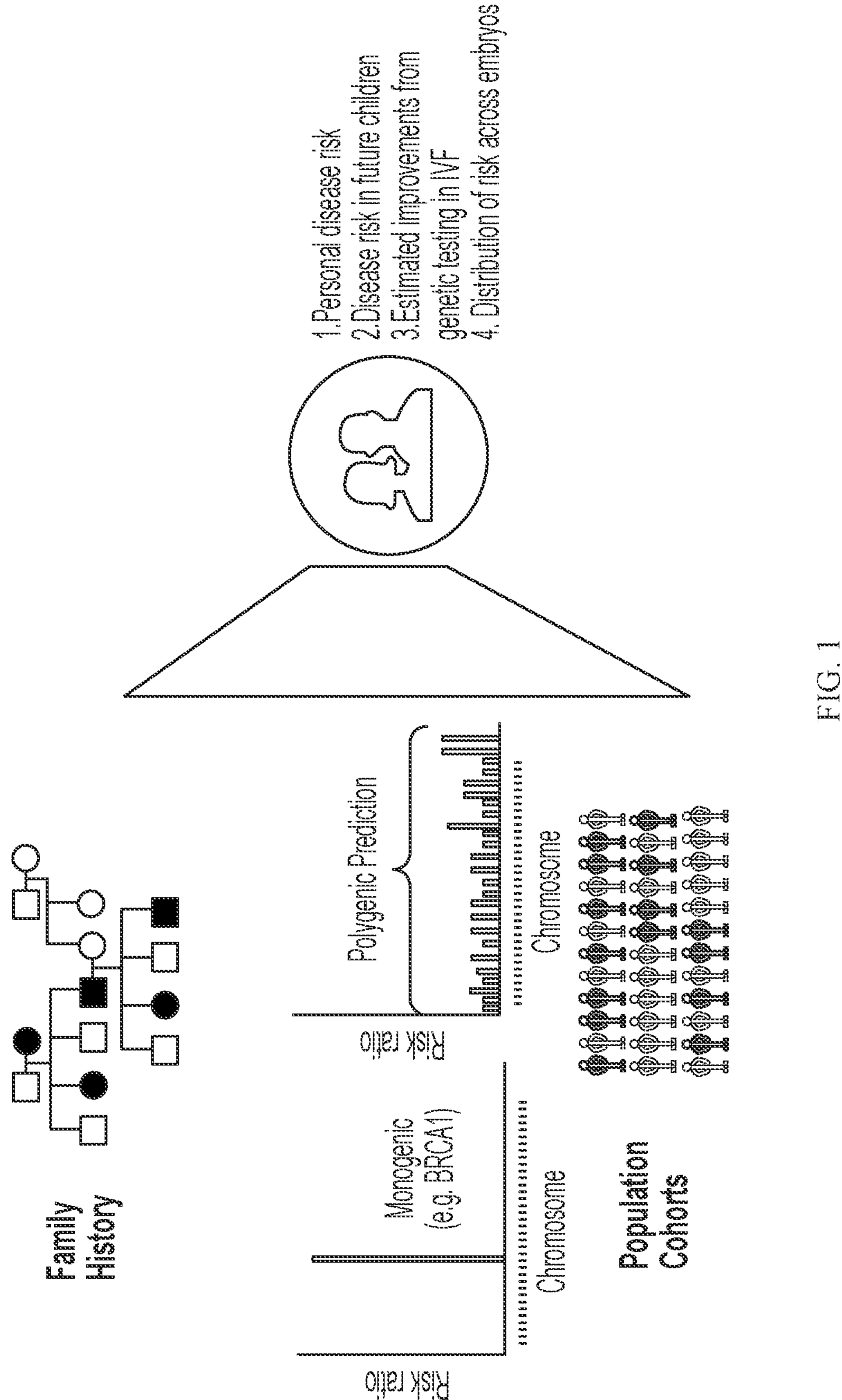
FIG. 1 depicts an exemplary methodology for predicting and reducing risk of disease.

Technical and scientific terms used herein have the meanings commonly understood by one of ordinary skill in the art to which the present invention pertains, unless otherwise defined. Materials to which reference is made in the following description and examples are obtainable from commercial sources, unless otherwise noted.

As used herein, the singular forms "a," "an," and "the" designate both the singular and the plural, unless expressly stated to designate the singular only.

The term "about" means that the number comprehended is not limited to the exact number set forth herein, and is intended to refer to numbers substantially around the recited number while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

The term "gene" relates to stretches of DNA or RNA that encode a polypeptide or that play a functional role in an organism. A gene can be a wild-type gene, or a variant or mutation of the wild-type gene. A "gene of interest" refers to a gene, or a variant of a gene, that may or may not be known to be associated with a particular phenotype, or a risk of a particular phenotype.

"Expression" refers to the process by which a polynucleotide is transcribed from a DNA template (such as into a mRNA or other RNA transcript) and/or the process by which a transcribed mRNA is subsequently translated into peptides, polypeptides, or proteins. Expression of a gene encompasses not only cellular gene expression, but also the transcription and translation of nucleic acid(s) in cloning systems and in any other context. Where a nucleic acid sequence encodes a peptide, polypeptide, or protein, gene expression relates to the production of the nucleic acid (e.g., DNA or RNA, such as mRNA) and/or the peptide, polypeptide, or protein. Thus, "expression levels" can refer to an amount of a nucleic acid (e.g. mRNA) or protein in a sample.

"Haplotype" refers to a group of genes or alleles that are inherited together, or expected to be inherited together, from a single antecedent (such as a father, mother, grandfather, grandmother, etc.). The term "antecedent" refers to a person from who a subject has descended, or in the case of an embryo from who a potential subject will have descended. In preferred aspects, the antecedent refers to a mammalian subject, such as a human subject.

Diseases and Methods

Provided are methods of identifying diseases, or a risk of having or inheriting a disease, caused in whole or in part by genetics. Genetic disorders can be caused by a mutation in one gene (monogenic disorder), by mutations in multiple genes (polygenic disorders), by a combination of gene mutations and environmental factors (multifactorial disorders), or by chromosome abnormalities (changes in the number or structure of entire chromosomes, the structures that carry genes). In some aspects, the disease is a polygenic disorder, a multifactorial condition, or a rare monogenic disorder (e.g., that has not previously been identified in the family).

Some aspects comprise determining whether an embryo is a carrier for a genetic disorder. Some aspects comprise determining whether the embryo will develop into a subject that has, or is likely to have, a genetic disorder. Some aspects comprise determining whether the embryo will develop into a subject that has, or is likely to have, one or more phenotypes associated with a genetic disorder.

Some aspects comprise selecting an embryo based on the genetic makeup of the embryo. For instance, some aspects comprise selecting an embryo with a low risk of carrying a genetic disorder. Some aspects comprise selecting an embryo that, if it develops into a child or adult, will have a low risk of having a genetic disorder. Some aspects comprise implanting the selected embryo into the uterus of a subject. Such methods are described in greater detail in, e.g., Balaban et al, "Laboratory Procedures for Human In Vitro Fertilization," *Semin. Reprod. Med.,* 32(4): 272-82 (2014), which is incorporated herein by reference in its entirety.

Some aspects comprise evaluating the disease risk associated with an embryo formed using one or more sperm donors. Some aspects comprise selecting a sperm donor based on the risk of disease. Some aspects comprise fertilizing an egg in vitro with the selected sperm.

Some aspects comprise determining a health report for an individual, e.g., based on the presence or absence of polygenic or rare monogenic variants. Some aspects comprise determining a distribution of disease probabilities, e.g., based on a polygenic risk score.

Diseases that can be screened are not limited. In some aspects, the disease is an autoimmune condition. In some aspects, the disease is associated with a particular HLA type. In some aspects, the disease is cancer. Exemplary conditions include coronary artery disease, atrial fibrillation, type 2 diabetes, breast cancer, age-related macular degeneration, psoriasis, colorectal cancer, deep venous thrombosis, Parkinson's disease, glaucoma, rheumatoid arthritis, celiac disease, vitiligo, ulcerative colitis, Crohn's disease, lupus, chronic lymphocytic leukemia, type 1 diabetes, schizophrenia, multiple sclerosis, familial hypercholesterolemia, hyperthyroidism, hypothyroidism, melanoma, cervical cancer, depression, and migraine. Some exemplary diseases comprise single gene disorders (e.g. Sickle cell disease, Cystic Fibrosis), disorders of chromosomal copy number (e.g. Turner Syndrome, Down Syndrome), disorders of repeat expansions (e.g. Fragile X Syndrome), or more complex polygenic disorders (e.g. Type 1 Diabetes, Schizophrenia, Parkinson's Disease etc.). Other exemplary diseases are described in PHYSICIANS' DESK REFERENCE (PRD Network 71st ed. 2016); and THE MERCK MANUAL OF DIAGNOSIS AND THERAPY (Merck 20th ed. 2018), each of which are herein incorporated by reference in their entirety. Diseases whose inheritance is complex by definition have multiple genetic loci contributing to disease risk. In these situations, a polygenic risk score can be calculated and used to stratify embryos into high risk and low risk categories

Embryo Genome Construction

Provided are novel and inventive methods related to embryo genome construction. In some aspects, the construction uses chromosomal length parental haplotypes and sparse genotyping of parents and embryos (e.g. using a SNP array or low-coverage DNA sequencing) to enable whole genome prediction in embryos. Such a hybrid approach can combine genetic information from parents and other relatives if available (e.g. grandparents and siblings) as well as haplotypes directly obtained (e.g. dense haplotype blocks) from DNA using molecular methods (e.g. Long Fragment Read technology, 10X Chromium technology, Minion system). Chromosome length haplotypes can be used to predict the genome of embryos in a setting of in-vitro fertilization. Such predicted genome sequences can be used to predict risk for disease, both by directly measuring the transmission of variants that cause Mendelian disorders and by constructing polygenic risk scores to predict the risk for disease.

In some aspects, the embryo genome is constructed using haplotypes from two or more antecedents. In some aspects, the embryo genome is constructed using both a paternal haplotype and a maternal haplotype. In some aspects, the haplotype is a grandpaternal haplotype. In some aspects, the haplotype is a grandmaternal haplotype. In some aspects, the embryo genome is constructed using a paternal haplotype, a maternal haplotype, and one or both of a grandpaternal haplotype and a grandmaternal haplotype. In some aspects sparse embryo genotypes are obtained from sequencing cell-free DNA in embryo culture medium, blastocele fluid or DNA obtained from trophectoderm cell biopsies of embryos.

Some aspects comprise determining one or more haplotypes used to construct the embryo genome. Such haplotypes can be determined, for example, based on the genome sequence of an antecedent subject. Some aspects comprise identifying the genome associated with the antecedent subject. Some aspects comprise performing whole genome sequencing on a biological sample obtained from an antecedent subject to identify the genome of the antecedent subject. Some aspects include using one or more sibling embryo(s) to determine the haplotypes. Such whole genome sequencing can be performed using any of a variety of techniques, such as standard, PCR-free, linked read (e.g., synthetic long read), or long read protocols. Exemplary sequencing techniques are disclosed, e.g., in Huang et al., "Recent Advances in Experimental Whole Genome Haplotyping Methods," *Int'l. J. Mol. Sci.,* 18(1944): 1-15 (2017); Goodwin et al, "Coming of age: ten years of next-generation sequencing technologies," *Nat. Rev. Genet.,* 17: 333-351 (2016); Wang et al., "Efficient and unique cobarcoding of second-generation sequencing reads from long DNA molecules enabling cost-effective and accurate sequencing, haplotyping, and de novo assembly," *Genome Res.,* 29(5): 798-808 (2019); and Chen et al., "Ultralow-input single-tube linked-read library method enables short-read second-generation sequencing systems to routinely generate highly accurate and economical long-range sequencing information," *Genome Res.,* 30(6): 898-909 (2020), each of which are incorporated herein by reference in their entireties.

Genome Phasing

Some aspects comprise phasing or estimating the antecedent genome to identify one or more haplotypes. Such phasing can be performed, for instance, using population-based and/or molecular based methods (such as linked read methods). Exemplary phasing techniques are disclosed, for instance, in Choi et al., "Comparison of phasing strategies for whole human genomes," *PLoS Genetics,* 14(4): e1007308 (2018); Wang et al., "Efficient and unique cobarcoding of second-generation sequencing reads from long DNA molecules enabling cost-effective and accurate sequencing, haplotyping, and de novo assembly," *Genome Res.,* 29(5): 798-808 (2019); and Chen et al., "Ultralow-input single-tube linked-read library method enables short-read second-generation sequencing systems to routinely generate highly accurate and economical long-range sequencing information," *Genome Res.,* 30(6): 898-909 (2020), each of which are incorporated herein by reference in their entireties.

In some aspects, phasing uses data generated from linked-read sequencing, long fragment reads, fosmid-pool-based phasing, contiguity preserving transposon sequencing, whole genome sequencing, Hi-C methodologies, dilution-based sequencing, targeted sequencing (including HLA typing), or microarray.

Some aspects include the use of sparse phased genotypes obtained independently to provide a scaffold to guide phasing. Computer software such as HapCUT, SHAPEIT, MaCH, BEAGLE or EAGLE can be used to phase an antecedent's genotype. In some instances, the computer program uses a reference panel such as 1000 Genomes or Haplotype Reference Consortium to phase the genotype. In some instances, phasing accuracy may be improved by the addition of genotype data from relatives such as grandparents, siblings, or children.

Predicting Embryo Genome Sequence

Some aspects comprise using phased parental genomes in combination with sparse genotyping of an embryo to predict the genome of an embryo, which can allow determination of the presence/absence of clinically relevant variants identified in the parents and in the embryo. This can be extended to include risk/susceptibility alleles identified in the parents and HLA types. In some aspects sparse genotyping is obtained using next-generation sequencing. Sparse genotyping is described in greater detail in Kumar et al., "Whole genome prediction for preimplantation genetic diagnosis," *Genome Med.,* 7(1): Article 35, pages 1-8 (2015); Srebniak et al., "Genomic SNP array as a gold standard for prenatal diagnosis of foetal ultrasound abnormalities," Molceular Cytogenet., 5: Article 14, pages 1-4 (2012); and Bejjani et al., "Clinical Utility of Contemporary Molecular Cytogenetics," *Annu. Rev. Genomics Hum. Genet.,* 9: 71-86 (2008), each of which are incorporated herein by reference in their entireties.

The sparse genotyping can be performed on an extracted portion of the embryo. Thus, some aspects comprise extracting or obtaining one or more cells from the embryo (e.g., via a biopsy). Some aspects comprise extracting or obtaining nucleic acids (e.g., DNA) from the embryo or from one or more cells from the embryo. Some aspects comprise extracting embryo material from an embryo culture medium.

Some aspects use sparse embryo genotypes as a scaffold for phasing antecedent subject genomes. Some aspects use information from one or more grandparental subjects (e.g., grandpaternal and/or grandmaternal subject(s)) to phase parental genomes. Some aspects use information from large reference panels (e.g., population based data) to phase parental genomes.

In some aspects, the embryo is reconstructed using biological sample(s) obtained from one or more antecedent subject(s). Exemplary biological samples include one or more tissues selected from brain, heart, lung, kidney, liver, muscle, bone, stomach, intestines, esophagus, and skin tissue; and/or one or more of a biological fluids selected from urine, blood, plasma, serum, saliva, semen, sputum, cerebral spinal fluid, mucus, sweat, vitreous liquid, and milk. Some aspects comprise obtaining the biological sample from the subject.

Some aspects comprise determining the transmission probability of one or more antecedent haplotypes. In some aspects, transmission of variants from one or more maternal heterozygous sites can involve sequencing the maternal genome, sequencing or genotyping one or more biopsies from an embryo, assembling or phasing the maternal DNA sample into haplotype blocks, utilizing the information from multiple embryos (e.g. parental support technology) to construct chromosome length haplotypes of parents, and predicting the inheritance or transmission of these haplotype blocks using a statistical method like a HMM. In some aspects the HMM can also predict transitions between haplotype blocks or correct errors in maternal phasing.

The approach to predict transmission of variants from one or more paternal heterozygous sites can involve sequencing the paternal genome, sequencing or genotyping one or more biopsies from an embryo, assembling or phasing the paternal DNA sample into haplotype blocks, utilizing the information from multiple embryos to improve the contiguity of the haplotype blocks to chromosome length, and predicting the inheritance or transmission of these haplotype blocks using a statistical method like a HMM. In some aspects the HMM can also predict transitions between haplotype blocks or correct errors in maternal phasing.

Situations where both mother and father are heterozygous can be predicted in the manner above. Embryo genotypes are trivially predicted where both parents are homozygous either for the same allele, or for a different allele.

In some aspects, transmission probability is determined using methods described in U.S. Application Ser. Nos. 11/603,406; 12/076,348; or 13/110,685; or in PCT Application Nos. PCT/US09/52730 or PCT/US10/050824, each of which are incorporated herein by reference in their entireties. In some aspects regions with a transmission probability of 95% or greater are used to construct the embryo genome.

In some aspects the embryo genome is constructed using one or more genes or genetic variants in the embryo. In some aspects the one or more genes or genetic variants are identified using sparse genotyping on an embryo. In some aspects, the sparse genotyping is performed using microarray technology.

In some aspects, the embryo genome is constructed using (i) the one or more genetic variants in the embryo, (ii) one or more antecedent haplotype(s) (e.g., a paternal haplotype and a maternal haplotype and (iii) a transmission probability of the one or more haplotypes (e.g. the paternal haplotype and the maternal haplotype). In some aspects the sparse genotyping is performed using next-generation sequencing.

Some aspects comprise embryo genome prediction that uses 1) whole genome sequences for both grandparents on each side of the family, 2) phased whole genome sequences from each parent, 3) sparse genotypes measured by array for the parents, and 4) sparse genotypes of the embryo. Without being bound by theory, it is believed that a prediction accuracy of 99.8% across 96.9% of the embryo genome can be achieved using such methods for a well-studied CEPH family.

Some aspects include phasing of parental genomes using 1) WGS for a single grandparent 2) sparse parental genotypes measured by an array and 3) a haplotype resolved reference panel. Some aspects include phasing of parental genomes using 1) sparse parental genotypes measured by an array and 2) a haplotype resolved reference panel (e.g. 1000 Genomes). Some aspects include phasing of parental genomes using only a haplotype resolved reference panel (e.g. 1000 Genomes).

Risk Determination

Also provided are methods of determining a disease risk associated with an embryo (e.g., based on a constructed genome for the embryo). Some aspects comprise determining whether a disease causing genetic variant from an antecedent genome has been transmitted to the embryo. Some aspects comprise determining whether a haplotype (e.g., associated with a disease causing genetic variant) has been transmitted to the embryo. Some aspects comprise determining the presence or absence of genetic variants causing disease or increasing disease susceptibility including (but not limited to) single nucleotide variants (SNVs), small insertions/deletions, and copy number variants (CNVs). Some aspects comprise determining the presence or absence of disease-associated HLA types in embryos.

In some aspects, a phenotype risk in embryos can be determined using one or more diseases (e.g., a set of diseases), which can be ranked based on the age of onset and disease severity. In some aspects, the disease ranking can be combined with polygenic risk prediction to rank embryos by potential disease risk.

Some aspects comprise determining that an embryo has a 10%, 20%, 30%, 40%, 50%, 60%, 70%, 80%, 90%, 95%, 99%, or more disease risk. Some aspects comprise determining that an embryo has a 90%, 80%, 70%, 60%, 50%, 40%, 30%, 20%, 10%, 5%, 1%, or less disease risk. Some aspects comprise selecting an embryo based on the disease risk (e.g., selecting an embryo that has a relatively low disease risk) and/or based on the presence or absence of a particular gene variant (e.g., SNV, haplotype, insertion/deletion, and/or CNV).

In some aspects, the disease risk associated with an embryo is determined using a polygenic risk score. In some aspects, the polygenic risk score (also referred to as "PRS") is determined by summing an effect across sites in a disease model. In some aspects, the polygenic risk score is determined using population data. For instance, population data can involve allele frequencies, individual genotypes, self-reported phenotypes, clinically reported phenotypes (e.g. ICD-10 codes), and/or family history (e.g., derived from related individuals in one or more population databases) information. Such population data can be obtained from any of a variety of databases, including the United Kingdom (UK) Biobank (which has information on ~300,000 unrelated individuals); various genotype-phenotype datasets that are part of the Database of Genotype and Phenotype (dbGaP) maintained by the National Center for Biotechnology Information (NCBI); The European Genome-phenome Archive; OMIM; GWASdb; PheGenl; Genetic Association Database (GAD); and PhenomicDB.

In some aspects, the disease risk is determined based on a polygenic risk score cutoff value. For instance, such a cutoff can include the highest about 1% in a PRS distribution, the highest about 2% in a PRS distribution, the highest about 3% in a PRS distribution, the highest about 4% in a PRS distribution, or the highest 4% in a PRS distribution. Preferably the cutoff is based on the highest 3% in a PRS distribution. The polygenic risk score cutoff can also be determined based on an absolute risk increase, e.g., of about 5%, about 10%, or about 15%. Preferably, the polygenic risk score cutoff is determined based on an absolute risk increase of 10%.

Some aspects comprise using a predicted embryo genome to estimate a phenotypic risk. In some aspects, the risk estimation uses 1) the predicted genome of an embryo, 2) genotypes of parents at sites of interest (i.e. variants included in a polygenic risk score) where a prediction is not made in the embryo and 3) allele frequencies in a reference cohort (e.g. UKBB) at sites of interest (e.g., variants included in the polygenic risk score) where a prediction is not made in the embryo.

Some aspects comprise determining risk based on the transmission probability of one or more genetics variants (e.g., based on antecedent haplotypes). Some aspects comprise determining a combined risk associated with an embryo based on the polygenic disease risk and the transmission probability of one or more genetic variants (e.g., transmission of a monogenic disease causing genetic variant(s) and/or haplotypes from the paternal genome and/or maternal genome to the embryo).

Figure 2:
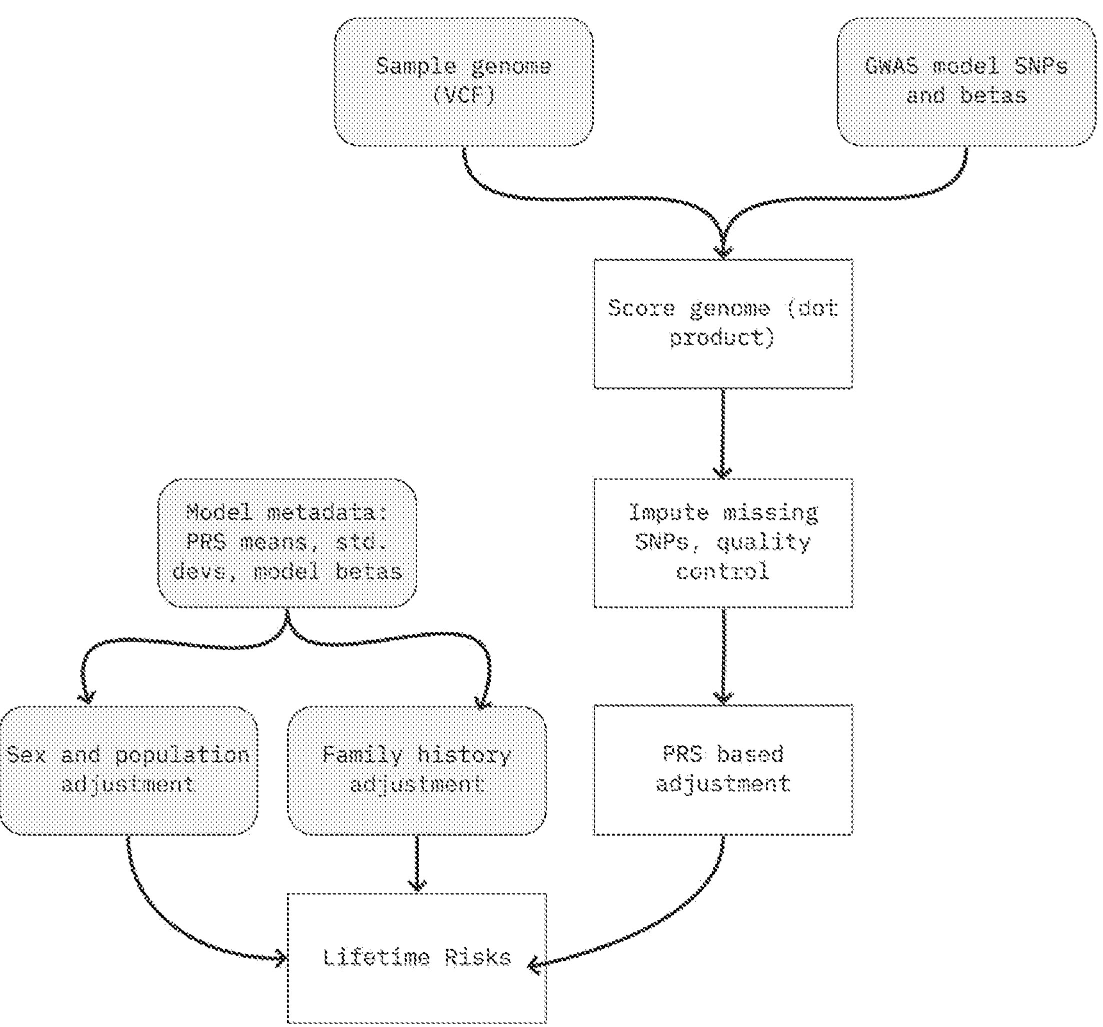
FIG. 2 depicts a flow chart providing an exemplary methodology for determining a polygenic risk score.

A non-limiting exemplary system for predicting and reducing risk of disease is shown in FIG. 1. A non-limiting exemplary polygenic risk score workflow is shown in FIG. 2.

Donor Selection

Also provided are methods of selecting a sperm and/or egg donor. Estimates of a subject's risk to pass on disease to their offspring can be computed by simulating virtual children's genomes and calculating disease risk for each child. Some aspects comprise determining a disease risk of a prospective mother and one or more potential sperm donors. Some aspects comprise determining a disease risk of a prospective father and one or more potential egg donors.

Figure 3:
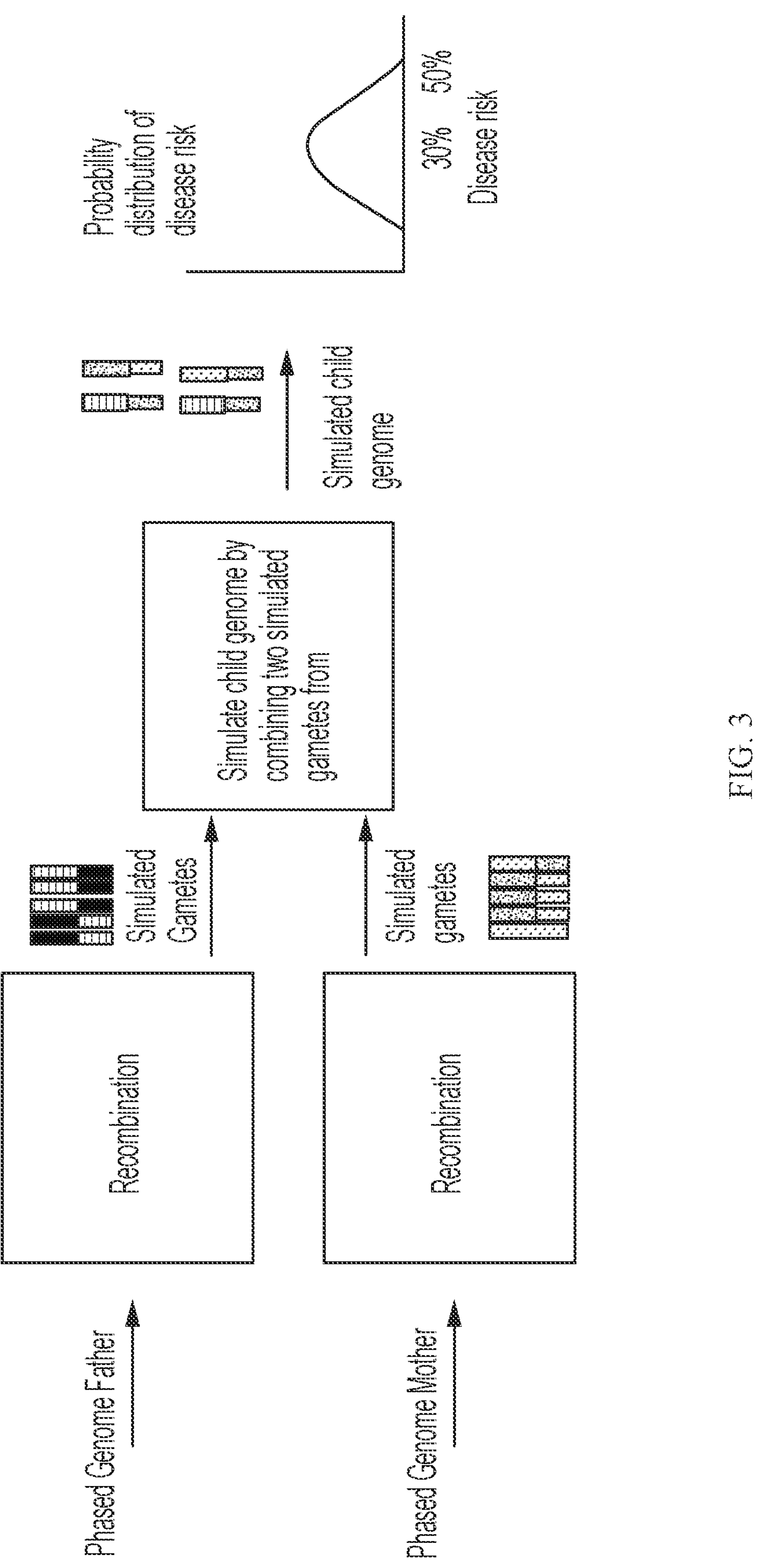
FIG. 3 depicts an exemplary methodology for determining disease risk in a child.

Some aspects comprise simulating gametes from a potential mother and father using phased parental genomes and simulated haplotype recombination sites, e.g., as determined using the HapMap database. Some aspects take into account the respective recombination rates during meiosis in the production of these gametes. In some aspects, these simulated gametes are combined with each other to result in numerous combinatorial possibilities to approximate the range of potential child genomes. Such an array of children's genomes can be transferred into an array of disease probabilities to predict the distribution of disease risk across each child. See FIG. 3.

Risk estimates as described herein (e.g., in the embryo genome construction section and/or Examples section) can be used in the context of family planning in embryo selection during an IVF cycle and/or sperm donor selection. In some embodiments, potential parents receive a report containing either individual risk estimates for multiple phenotypes across all available embryos or a range of risk values for each potential sperm donor. In some aspects, sperm donors are ranked based on disease risk for a condition or set of conditions. In some aspects, donors are selected using the python script disclosed in U.S. Provisional Application No. 63/062,044, filed on Aug. 6, 2020, or a modification thereof.

Some aspects comprise selecting an embryo based on the risk score. Some aspects comprise selecting an egg donor based on the risk score. Some aspects comprise selecting the sperm donor based on the risk score.

Implementation Systems

The methods described here can be implemented on a variety of systems. For instance, in some aspects the system (e.g., for genome embryo construction, donor selection, risk determination, and/or performing health reports) includes one or more processors coupled to a memory. The methods can be implemented using code and data stored and executed on one or more electronic devices. Such electronic devices can store and communicate (internally and/or with other electronic devices over a network) code and data using computer-readable media, such as non-transitory computer-readable storage media (e.g., magnetic disks; optical disks; random access memory; read only memory; flash memory devices; phase-change memory) and transitory computer-readable transmission media (e.g., electrical, optical, acoustical or other form of propagated signals—such as carrier waves, infrared signals, digital signals).

The memory can be loaded with computer instructions to train a model as needed (e.g., to identify disease risk). In some aspects, the system is implemented on a computer, such as a personal computer, a portable computer, a workstation, a computer terminal, a network computer, a supercomputer, a massively parallel computing platform, a television, a mainframe, a server farm, a widely-distributed set of loosely networked computers, or any other data processing system or user device.

The methods may be performed by processing logic that comprises hardware (e.g. circuitry, dedicated logic, etc.), firmware, software (e.g., embodied on a non-transitory computer readable medium), or a combination of both. Operations described may be performed in any sequential order or in parallel.

Generally, a processor can receive instructions and data from a read only memory or a random access memory or both. A computer generally contains a processor that can perform actions in accordance with instructions and one or more memory devices for storing instructions and data. Generally, a computer will also include, or be operatively coupled to receive data from or transfer data to, or both, one or more mass storage devices for storing data, e.g., magnetic disks, magneto optical disks, optical disks, or solid state drives. However, a computer need not have such devices. Moreover, a computer can be embedded in another device, e.g., a smart phone, a mobile audio or media player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including, by way of example, semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Figure 21:
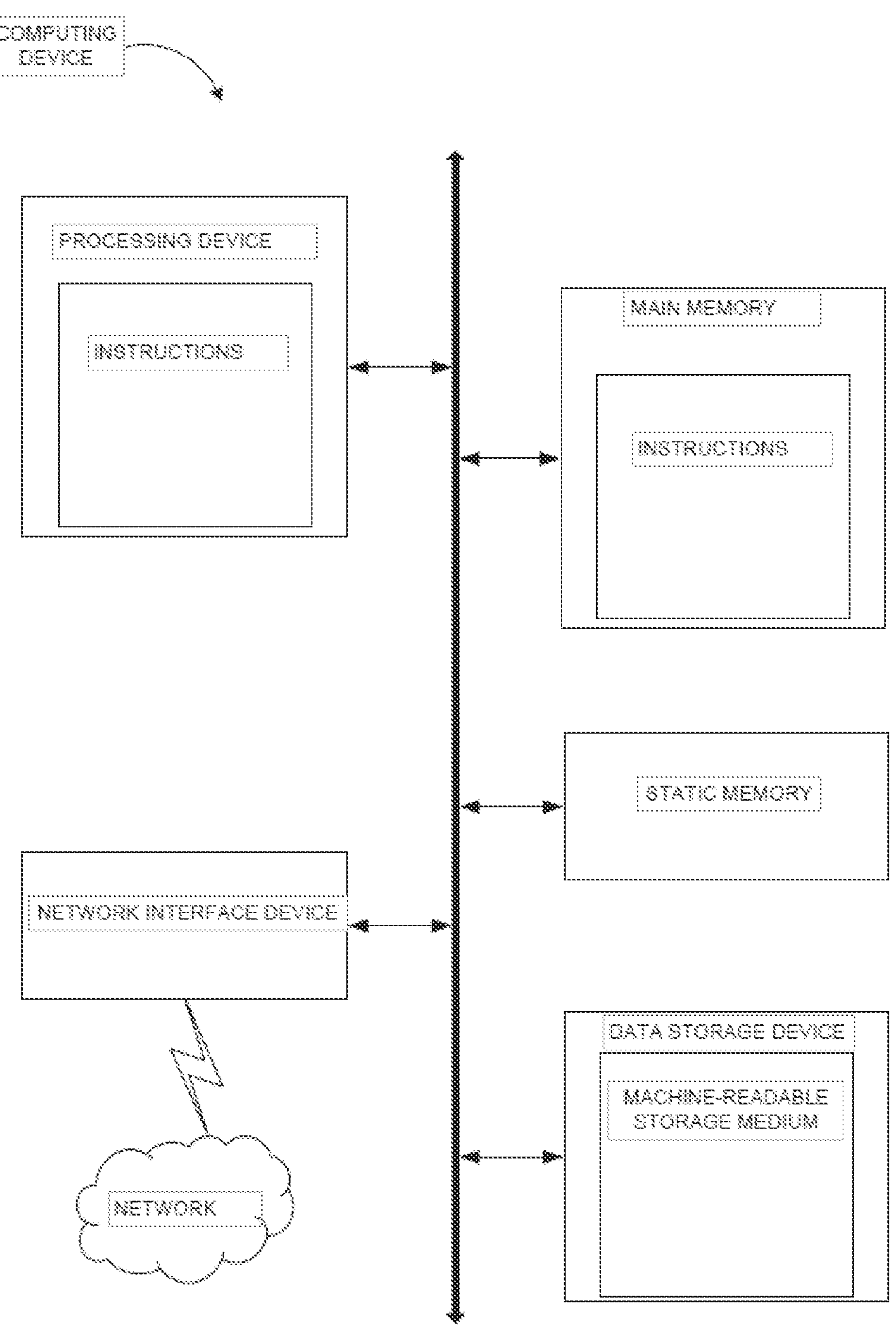
FIG. 21 is a block diagram of an example computing device.

An exemplary implementation system is set forth in FIG. 21. Such a system can be used to perform one or more of the operations described here. The computing device may be connected to other computing devices in a LAN, an intranet, an extranet, and/or the Internet. The computing device may operate in the capacity of a server machine in client-server network environment or in the capacity of a client in a peer-to-peer network environment.

The following examples are provided to illustrate the invention, but it should be understood that the invention is not limited to the specific conditions or details of these examples.

EXAMPLES

Example 1: Parental Genome Phasing for Parental Recurrence Risk Assessment and Disease Prediction in Embryos for Pre-Implantation Genetic Testing—Use in Predicting Embryo Genome Sequence in In Vitro Fertilization (IVF)

Figure 4:
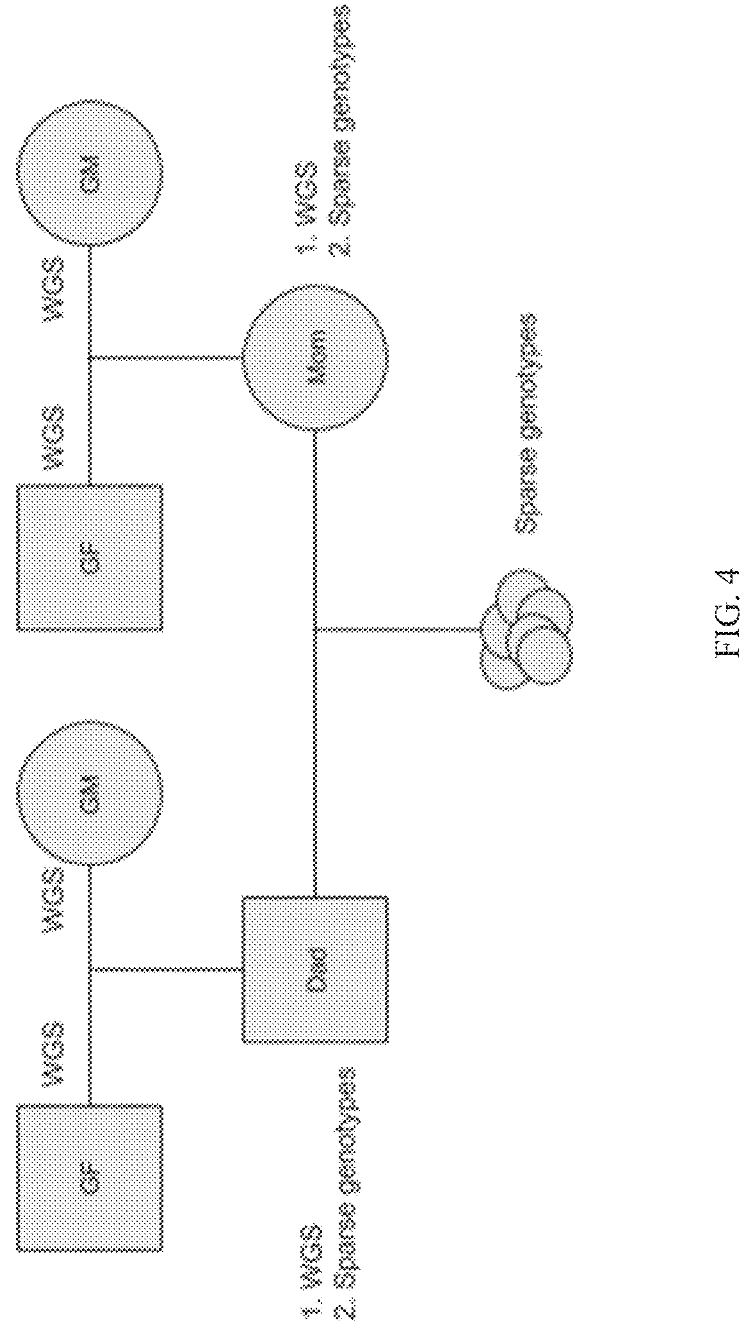
FIG. 4 depicts exemplary inputs that can be used to determine disease probabilities.

Embryo coverage and accuracy was calculated using three different protocols. In accordance with a first protocol, embryo genome prediction used 1) whole genome sequence (WGS) for both grandparents on each side of the family, 2) phased WGS from each parent, 3) sparse genotypes measured by array for the parents, and 4) sparse genotypes of the embryo (FIG. 4). The protocol achieved a prediction accuracy of 99.8% across 96.9% of the embryo genome for a well-studied CEPH family. (Also contemplated is a protocol that uses 1) WGS for a single grandparent 2) sparse parental genotypes measured by an array and 3) a haplotype resolved reference panel)

In accordance with a second protocol, embryo prediction used 1) sparse parental genotypes measured by an array and 2) a haplotype resolved reference panel (e.g. 1000 Genomes).

In accordance with a third protocol, embryo prediction used only a haplotype resolved reference panel (e.g. 1000 Genomes).

Results from all three protocols are shown in Table 1 below. PRS shows results for ~1.4 million sites important in disease risk prediction.

TABLE 1

Embryo coverage and accuracy achieved with various phasing strategies

| Phasing strategy | Embryo Coverage | | Accuracy | |
|---|---|---|---|---|
| Grandparents + reference panel | Total | 91.46% | Total | 98.04% |
| | Hets | 85.27% | Hets | 98.33% |
| | PRS | 98.73% | PRS | 99.23% |
| Sparse genotype scaffold + reference panel | Total | 90.96% | Total | 97.5% |
| | Hets | 84.32% | Hets | 97.23% |
| | PRS | 98.90% | PRS | 98.91% |
| Reference panel only | Total | 87.07% | Total | 97.89% |
| | Hets | 76.92% | Hets | 98.06% |
| | PRS | 95.30% | PRS | 99.16% |

Example 2: Using Predicted Embryo Genome to Estimate Phenotype Risk

The probability of possible genotypes (AA, AB, BB) given the parental genotypes (M,D) is used at sites not predicted in the embryo genome (see Equation 1 below). Where parental genotypes are unavailable, cohort affect allele frequencies ($AF_{EA}$) are used (Equation 2)

$$\beta * P(AA|M, D) + \beta * P(AB|M, D) + \beta * P(BB|M, D) \quad \text{Equation 1}$$

$$2 * \beta * AF_{EA} \quad \text{Equation 2}$$

The risk score percentile in which an embryo falls within 3% of the true score for 27 out of 30 (90%) models was predicted.

A separate process involved using 1) the predicted genome of an embryo, and 2) allele frequencies in reference cohort (e.g. UKBB) at sites of interest (i.e. variants included in the polygenic risk score) where a prediction is not made in the embryo. Allele frequencies were used as described above in equation 2. Using this process, the risk score percentile which an embryo falls within 23 out of 30 (77%) models was predicted. All 30 predicted scores fall within 5% of the true score when parental genotypes were incorporated.

Example 3: Estimating and Improving Phenotype Risk Estimation Using Polygenic Risk Models

Statistical Framework

The workhorse model for disease simulations and empirical analysis is the threshold liability model. Diseases are considered to have a genetic component $g \sim N(0, h^2)$ where $h^2$ is the narrow sense heritability and an error component $\epsilon \sim N(0,1-h^2)$. The hypothesized liability l is given by $$l = g + \epsilon \sim N(0, 1)$$

is called the latent liability and samples are hypothesized to have risk on the latent liability scale. The threshold T is estimated from the disease prevalence p such that $\mathbb{P}(l>T)=p$, which is computed from the distribution of the standard normal random variable. Without being bound by theory, it is believed that all people affected by the disease have l>T.

Simulating families involves simulating genetic liabilities which are modeled as the sum of three components: two genetic components—the part measured by PRS, the "unmeasured" part that is simply the residual genetic risk, and irreducible non-genetic error. The latent genetic risk g from above can be broken down to $$g = g_R + g_U$$

defined so that $$g_U = g - g_R$$

This last component is uncorrelated between family members. On the other hand, if the variance explained by the PRS on the liability scale is $\sigma^2$, and $g_{R,i}$ and $g_{R,j}$ are the PRS component of the liability of two first degree relatives, then the covariance is given by $$\text{Cov}(g_{R,i}, g_{R,j}) = \frac{1}{2}\sigma^2.$$

If $g_{U,i}$ and $g_{U,j}$ are the residual unmeasured component of the liability of two first degree relatives, and $h^2$ is the heritability of the trait, then the covariance is given by $$\text{Cov}(g_{U,i}, g_{U,j}) = \frac{1}{2}(h^2 - \sigma^2).$$

If $g_i$ are the children of $g_1$ and $g_2$, then $$E[g_i] = \frac{g_1 + g_2}{2}.$$

For two first degree relatives i and j with liabilities $$l_i = g_{R,i} + g_{U,i} + \epsilon_i$$

$$l_j = g_{R,j} + g_{U,j} + \epsilon_i$$

we can see that $$\mathrm{Cov}(l_i, l_j) = \frac{1}{2}h^2$$

because the error terms are uncorrelated.

IVF Embryo Selection Simulation

IVF simulations were conducted to answer the following question: given a set of n embryos and a clinical phenotype of interest, how much less likely is the embryo with the minimum polygenic risk score to develop the disease over its lifetime than a randomly chosen embryo? In other words, what is the relative risk reduction of the selection?

To answer this question, a two-step procedure was used to generate the parameters for parents and subsequently their children. This procedure or a modification thereof will be used in simulations that test the effectiveness of donor selection and IVF embryo selection.

The following inputs were used in the embryo selection model: $\sigma^2$, the variance explained by a polygenic risk score on the liability scale; $h^2$, the additive heritability of a trait on the liability scale; p, the lifetime prevalence of a trait.

The output from this simulation is the risk reduction across a different number of embryos available, which allows a prospective couple doing IVF to target which diseases can be meaningfully screened.

Procedure

Step 1. For each parent, generate a PRS $g_R$ with distribution $N(0, \sigma^2)$ if drawn from the general population or some other distribution such as a shift in mean or a truncated normal to represent elevated risk from family history. A residual unmeasured genetic risk $g_U$ with distribution $N(0, h^2-\sigma^2)$ or something else as above.

Step 2. Simulate n children by computing $l_1, \ldots, l_n$:

compute the midparent mean PRS from the two parents:

$$M_R = \frac{g_{R,1} + g_{R,2}}{2}$$

compute the midparent mean residual genetic risk:

$$M_U = \frac{g_{U,1} + g_{U,2}}{2}$$

For each child, compute independent error $\epsilon_i$ with distribution $N(0,1-h^2)$.

For each child, compute an independent PRS recombination $$R_{P,i} \sim N\left(0, \frac{1}{2}\sigma^2\right)$$

For each child, compute an independent unmeasured/residual risk from recombination $$R_{U,i} \sim N\left(0, \frac{1}{2}(h^2 - \sigma^2)\right)$$

Compute liability for child i by summing $$l_i = M_R + M_U + R_{P,i} + R_{U,i} + \epsilon_i$$

Step 3. To determine the risk reduction, one simulates over a range of n=3,4, . . . ,10 many millions of families. For each family one sees if the liability $l_{min}$ of the embryo with the minimum PRS exceeds threshold $t=\Phi^{-1}(1-p)$ where $\Phi$ is the cumulative distribution function of the standard normal.

Statistical Note

As an addendum, one can justify the form of $R_{P,i}$ and $R_{U,j}$. To show that the covariances between siblings and between children and parents are correct, note that $$\begin{aligned} \mathrm{Cov}(g_{R,i}, g_{R,j}) &= \mathrm{Cov}(M_R + R_{U,i}, M_R + R_{U,j}) \\ &= \mathrm{Cov}(M_R, M_R) + 2\cdot\mathrm{Cov}(M_R, R_{U,i}) + \mathrm{Cov}(R_{U,i}, R_{U,j}) \\ &= \frac{1}{2}\sigma^2. \end{aligned}$$

since the latter two terms are 0. The same calculation works for the unmeasured genetic risk, i.e.

$$\mathrm{Cov}(g_{U,i}, g_{U,j}) = \frac{1}{2}(h^2 - \sigma^2).$$

so for $g=g_{R,i}+g_{U,i}$, $$\mathrm{Cov}(g_i, g_j) = \frac{1}{2}h^2$$

A similar set of calculations show that the parent-child covariance also satisfies the right equation.

Figure 5:
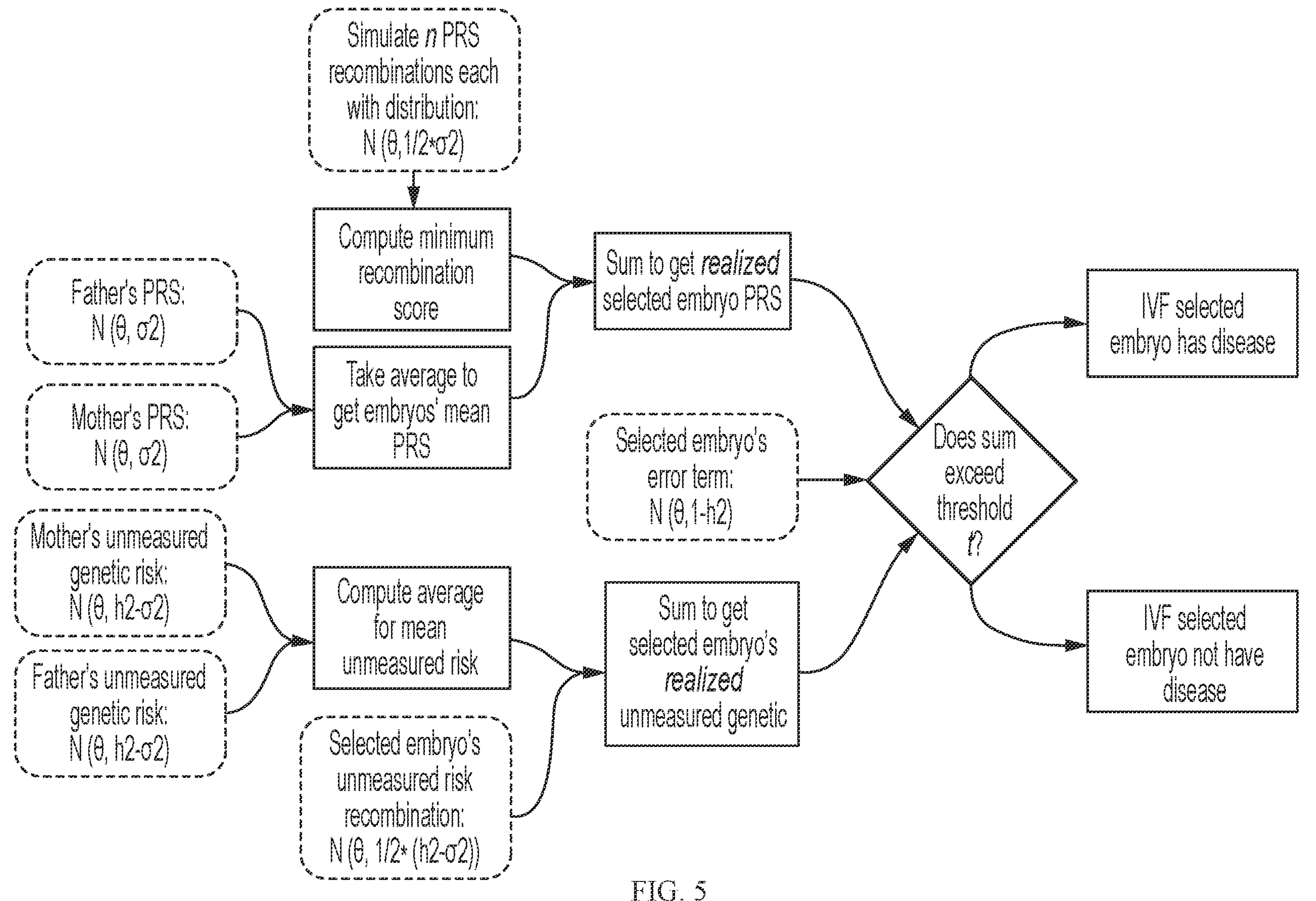
FIG. 5 depicts a flow chart showing an exemplary methodology for selecting an embryo based on the likelihood of disease.
Figure 6:
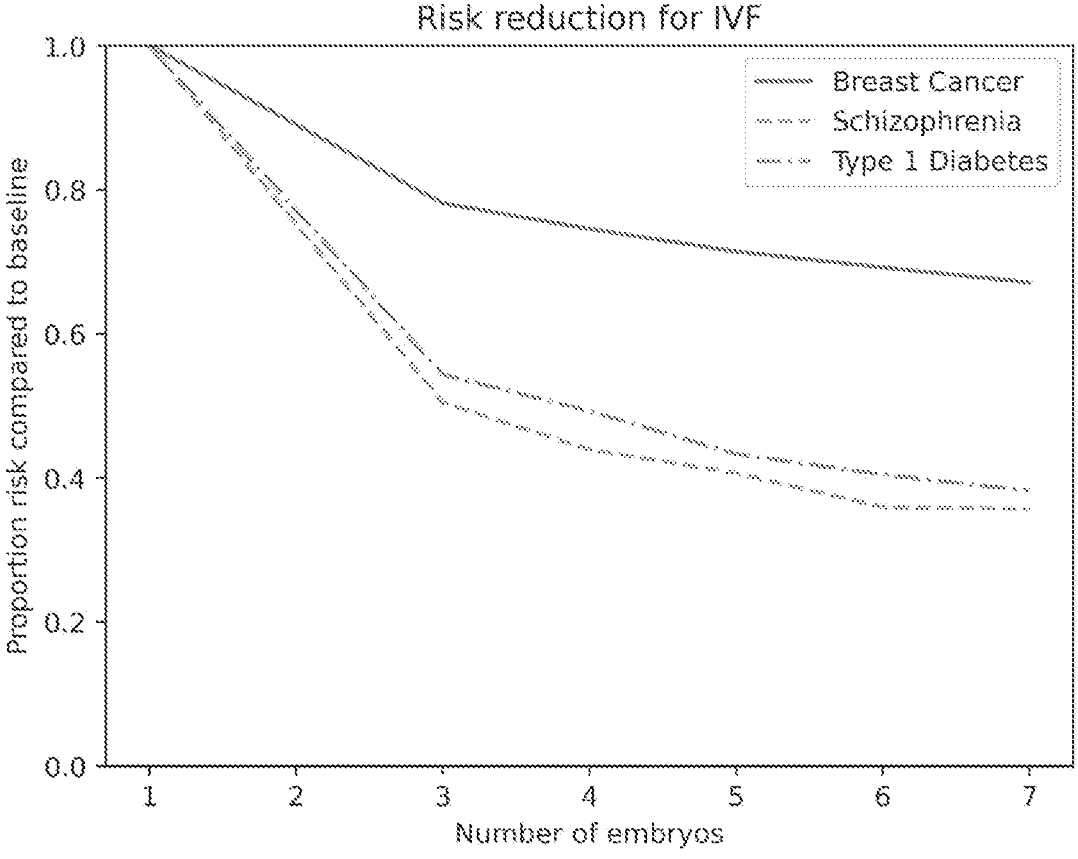
FIG. 6 provides a graphical representation of risk reduction curves associated with particular diseases.

This procedure can be viewed schematically in FIG. 5. An example of the risk reduction curves with inputs is shown in FIG. 6. The variance explained by the polygenic risk score is shown in Table 2 below, in which "h2_lee" is the variance.

TABLE 2

Variance explained by polygenic risk score for a variety of disorders

| Phenotype | $h^2$_lee | Prevalence | Diseasetype | heritability |
|---|---|---|---|---|
| AMD | 0.017064 | 0.0655 | Other | 0.50 |
| Breast cancer | 0.026747 | 0.1240 | Cancer | 0.31 |
| Prostate cancer | 0.051717 | 0.1160 | Cancer | 0.58 |

TABLE 2-continued

Variance explained by polygenic risk score for a variety of disorders

| Phenotype | $h^2$_lee | Prevalence | Diseasetype | heritability |
|---|---|---|---|---|
| CLL | 0.045575 | 0.0057 | Cancer | 0.60 |
| Psoriasis | 0.079081 | 0.0400 | Autoimmune | 0.75 |
| Rheumatoid arthritis | 0.017422 | 0.0140 | Autoimmune | 0.60 |
| Celiac disease | 0.246643 | 0.0100 | Autoimmune | 0.80 |
| Crohn's disease | 0.021475 | 0.0050 | Autoimmune | 0.80 |
| Type 1 Diabetes | 0.098359 | 0.0050 | Autoimmune | 0.72 |
| Type 2 Diabetes | 0.022617 | 0.2570 | Other | 0.50 |
| Atrial Fibrillation | 0.014569 | 0.2720 | Other | 0.67 |
| Bipolar disorder | 0.030115 | 0.0250 | Psychiatric | 0.55 |
| Schizophrenia | 0.035857 | 0.0050 | Psychiatric | 0.80 |
| Vitiligo | 0.062567 | 0.0200 | Autoimmune | 0.50 |
| Inflammatory Bowel Disease | 0.022788 | 0.0200 | Autoimmune | 0.50 |

Donor Families with Simulation

Figure 7:
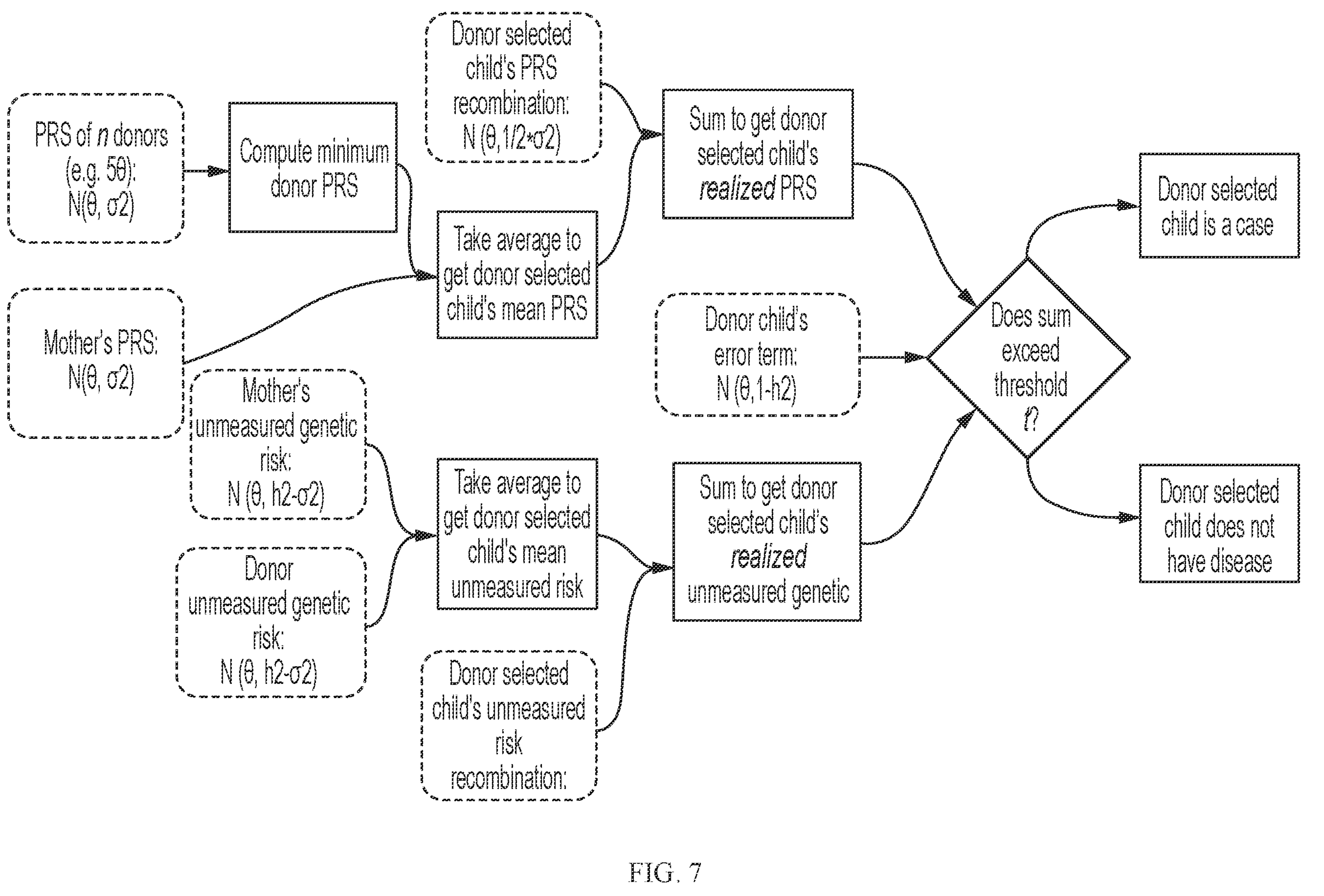
FIG. 7 depicts a flow chart providing an exemplary methodology for selecting a sperm donor.

To identify donors with a lower risk, the following were performed: (1) Calculate prospective mother's polygenic risk score, (2) Calculate polygenic risk scores across N number of donors, and (3) choose the donor with lowest polygenic risk score. The procedure is essentially the same as above, except two steps are changed: First, number of donors are simulated (n=10, 20, 30, . . . , 100), and the polygenic risk score is minimized over the donors' polygenic risk score, rather than minimizing the recombination. A flow chart for the method is shown in FIG. 7.

Figure 8:
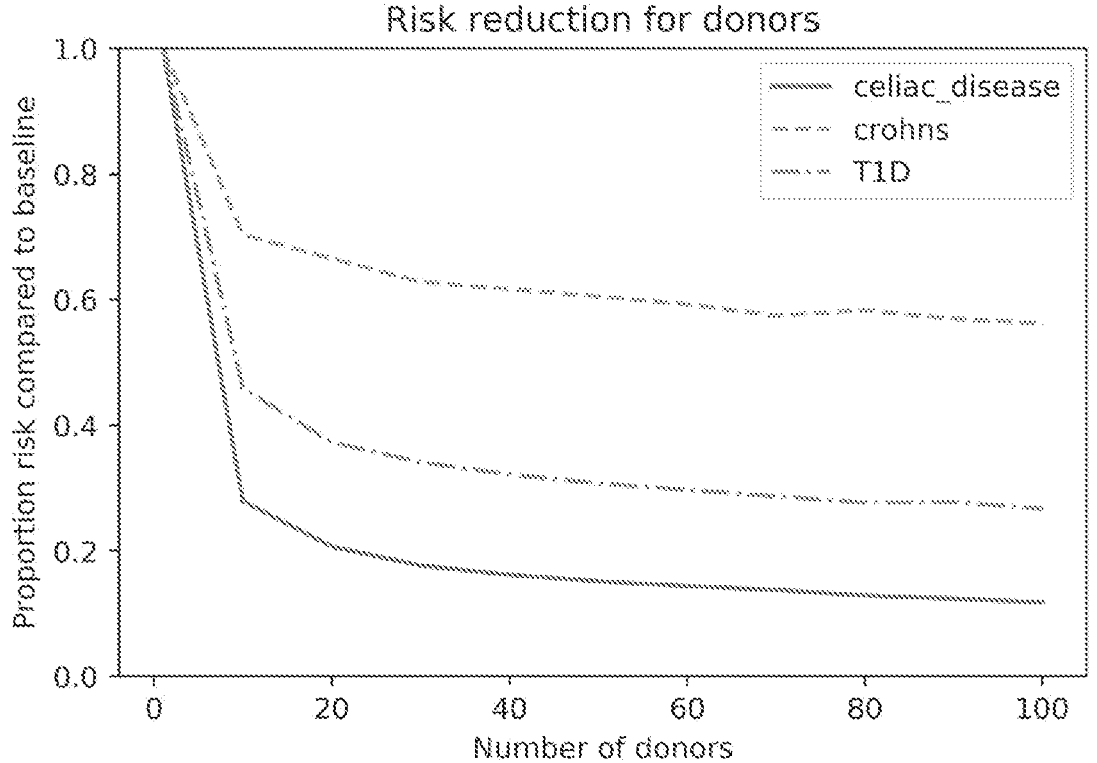
FIG. 8 provides a graphical representation of risk reduction curves produced for a number of donors on some autoimmune disorders.

The following inputs were used: $\sigma^2$, the variance explained by a PRS on the liability scale; $h^2$, the additive heritability of a trait on the liability scale; p, the lifetime prevalence of a trait. The output from this simulation is the risk reduction across different numbers of donors available over which to minimize, which allows a client using sperm or egg donor to target which diseases can be meaningfully screened. With the same example inputs as above, risk reduction curves were produced for different number of donors on some autoimmune disorders, which are shown in FIG. 8.

Additional Embryo Selection Following Donor Selection

An additional application of donor selection involves first selection of a donor and subsequently selection of an embryo with lower disease risk. More particularly, disease risk information is provided to a subject (e.g., a female subject) interested in using donor sperm for a child. First, using her genetic test results and family history, multiple gametes are simulated and combined with simulated sperm samples to obtain a risk of known genetic causes of heart disease. This is her "personalized risk" to have a child with this condition and is a refinement of the "baseline risk." Second, using genetic information from various donors as well as information on which variants are phased with each other, a range of disease probabilities assuming gametes from individual donors is calculated. Finally, assuming a donor is chosen, multiple embryos (E1, E2, E3) fall within a distribution of disease risk. See FIG. 9.

The methods can be used in the context of family planning during sperm donor selection. Potential parents can indicate phenotypes that are of particular interest to them and risk scores for those phenotypes can be generated for each of the donors. Those scores are used to predict disease risk in potential children for each of the sperm donors. A report containing these risk values can be given to the parents allowing them the option to select a donor that would reduce the risk of phenotypes of interest.

Family History

Family history can be incorporated into predicting risk for a disease. In the UK Biobank, there are some diseases with parent and sibling self-reported disease status: diabetes, heart disease, Alzheimer's, Parkinson's, breast cancer, and a handful of others. Moreover, there are over 10,000 sibling pairs and a large number of half-sibling or other second degree relative pairs. A model was built with a binary variable for family history which means: (i) in the set of diseases in the UK Biobank with self-reported family history, a sibling or parent with the disease; or (ii) for any other disease, for all samples with first degree relative in the UK Biobank. Given this definition for the "has_family_history" dummy, for each condition-on the appropriate cohort-a logistic regression was run using the formula:

$$\log(P/(1-P))=\text{beta\_1}*PRS+\text{beta\_2}*\text{sex\_male}+\text{beta\_3}*\text{has\_family\_history}.$$

To summarize, the inputs included: Data from biobanks which contain self-reported family history of disease and also pairs of first degree relatives with medical records. The outputs included: Models from logistic regressions which incorporate PRS and family history to increase the accuracy of our predictions. The models were used to prioritize which patients are at higher risk for developing a disease over their lifetimes. An exemplary output is set forth below in Table 3, in which beta_1 (PRS), beta_2 (sex dummy) and beta_3 (family history dummy) are estimated for a number of conditions.

TABLE 3

Data from logistical regression models that incorporate PRS

| Condition | Prs beta | Male | Has family history | Prevalence with history | Prevalence without history | Crude_ log_odds |
|---|---|---|---|---|---|---|
| Schizophrenia | 0.703300 | 0.546721 | 1.988776 | 0.063830 | 0.002133 | 3.462407 |
| Psoriasis | 0.552345 | 0.225942 | 1.024280 | 0.052381 | 0.014833 | 1.300528 |
| Celiac disease | 0.997422 | −0.694081 | 1.844601 | 0.099476 | 0.006963 | 2.757061 |
| Prostate Cancer | 0.509015 | 0.000225 | 1.420281 | 0.156757 | 0.037106 | 1.573611 |
| Ovarian Cancer | 0.030965 | 0.000000 | 0.345591 | 0.015152 | 0.006963 | 0.785832 |
| IBD | 0.298633 | 0.145434 | 1.522124 | 0.067055 | 0.013687 | 1.644707 |
| Type 1 Diabetes | 1.327803 | 0.434760 | 1.082481 | 0.030769 | 0.002860 | 2.404156 |
| Bipolar disorder | 0.695677 | 0.044206 | 1.090088 | 0.026549 | 0.005448 | 1.605146 |
| Colorectal cancer | 0.183265 | 0.328794 | 0.586361 | 0.022814 | 0.011288 | 0.715390 |
| CLL | 0.695600 | 0.508648 | 0.694252 | 0.020000 | 0.002254 | 2.200862 |

TABLE 3-continued

Data from logistical regression models that incorporate PRS

| Condition | Prs beta | Male | Has family history | Prevalence with history | Prevalence without history | Crude_ log_odds |
|---|---|---|---|---|---|---|
| Rheumatoid arthritis | 0.430699 | −0.599616 | 0.633962 | 0.027027 | 0.012419 | 0.792506 |
| Crohn's disease | 0.370405 | 0.220103 | 2.097058 | 0.061069 | 0.005412 | 2.481016 |
| Ulcerative colitis | 0.391589 | 0.147064 | 1.172390 | 0.038136 | 0.009856 | 1.382084 |

Figure 10:
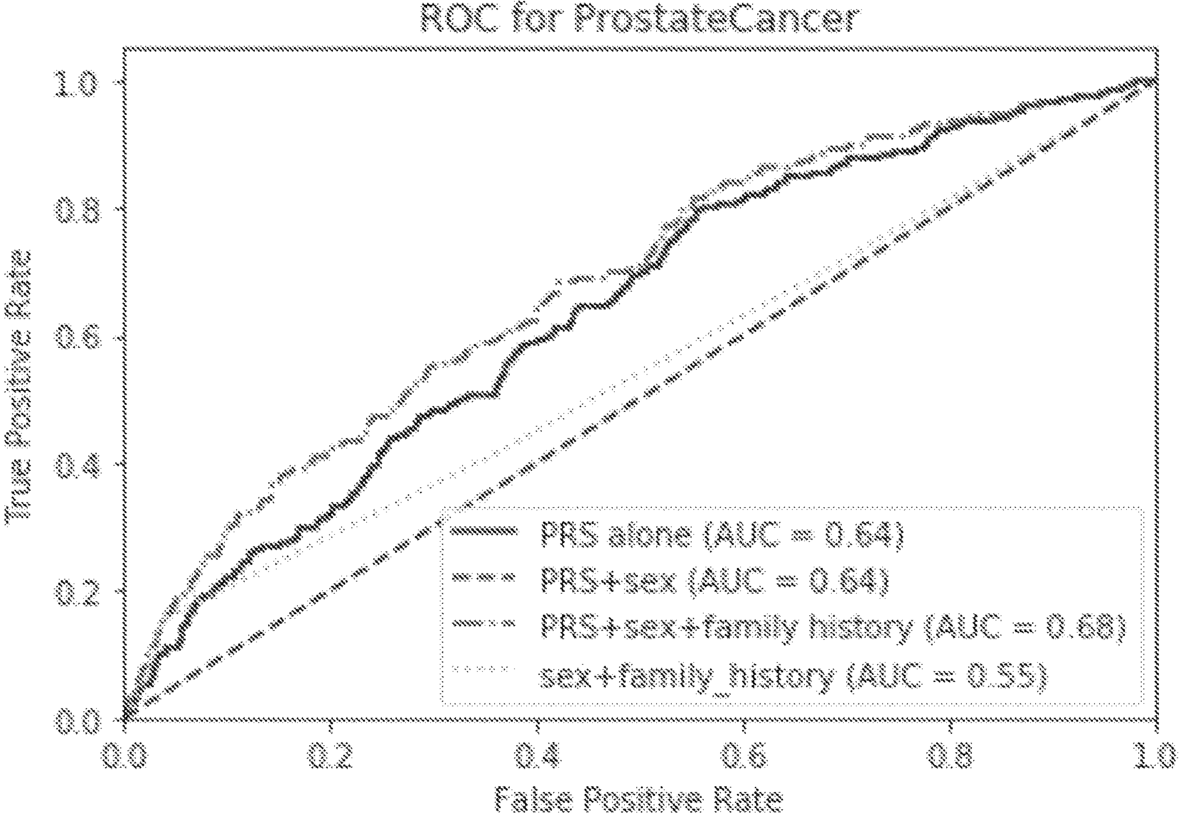
FIG. 10 provides a graphical representation of ROC curves showing an improvement in the predictive capabilities associated with determining a risk of prostate cancer.

The improvement in the predictions was quantified with ROC curves for prostate cancer when the has_family_history dummy is added to the logistic regression, as shown in FIG. 10.

Increased Model Sophistication

The models are made more sophisticated by incorporating 2nd and 3rd degree relatives, more complicated pedigrees, and/or related phenotypes. It was shown above how to simulate immediate families. To allow for 2nd degree family history incorporation, one can also simulate for each parent two additional family members. If $P_1$ is parent one with relatives $R_{1,i}$, then we can generate second degree family members by assuming $$Cov(P_1, R_{1,i}) = \frac{1}{2}\sigma^2$$

where $\sigma^2$ is the latent liability scale variance component for the PRS or unmeasured genetic risk $g_U$.

One can also add a further layer of complexity to the simulation: thresholds based on age and sex. If incidence of this disease differs by these variables, one can adjust the thresholds by which a sample in a family as having the disease is judged. As an example, suppose for type 2 diabetes, the prevalence in men aged 80+ is 20 percent, while the prevalence in women aged 55 is 4 percent. One could replace lifetime prevalence with lifetime risk by substituting empiric lifetime risk for disease in the model above. The thresholds for such samples will be $1-\Phi(0.20)$ and $1-\Phi(0.04)$ respectively, where $\Phi$ is the cumulative distribution function of the standard normal random variable. When one conditions on a family pedigree, they are conditioning on a set of samples $$s_i = g_{R,i} + g_{U,i} + \epsilon_i > T_i$$

exceeding their age- and sex-specific thresholds $T_i$.

Given a pedigree Ped with information about disease history, such as: father and paternal grandfather with the disease, three siblings without the disease, one can compute $$E(g_U|Ped)$$

A goal is to validate theoretical predictions on the quantity:

$$P(g_R + g_U + \epsilon > T|g_U = x)$$

which allows computation of an odds ratio.

HLA Phenotypes

Risk determination can involve phenotypes with a strong HLA component and for which the associated HLA allele is not well tagged by SNVs. However, this method can be applied to any condition for which there is a known disease association with an HLA allele of significant effect size and for which additional loci have been implicated. Examples of complex phenotypes with HLA involvement include (but are not limited to) psoriasis, multiple sclerosis, type 1 diabetes, inflammatory bowel disease, Crohn's disease, ulcerative colitis, vitiligo, celiac disease, and systemic lupus erythematosus.

The methods can be applied in multiple contexts including but not limited to individual disease risk prediction, risk reduction in both an embryo selection and sperm donor selection scenario and guidance in prescribing certain medications where multiple genetic factors, including HLA type, impacts likelihood of response or adverse drug reactions.

HLA typing results are obtained from DNA-based methods such as Sanger sequencing-based typing or derived from whole genome sequencing (WGS). First: A polygenic risk score is determined, e.g., using genome-wide association study (GWAS) effect sizes. One example is to sum the product of the effect size and the dose of the effect allele over all associated variants not in the MHC region. Secondly, relevant HLA alleles are combined or incorporated based on HLA-typing results (not tag SNPs) using one of the following methods.

Combining PRS and HLA OR: polygenic risk scores are calculated for all individuals in a validation cohort to obtain metadata (e.g. mean, standard deviation, etc.). Odds ratios (ORs) are obtained for HLA alleles with an established association with the phenotype of interest. The ORs derived from PRS of an individual compared to the validation cohort and HLA typing are combined as follows:

$$OR = OR_{HLA} * OR_{PRS} * OR_{demographic}$$

A risk ratio (RR) is calculated using the OR derived above and the prevalence of the disease in the validation cohort. This is then used to estimate lifetime risk of disease.

Incorporating HLA into PRS directly: HLA effect alleles are incorporated directly into the polygenic risk score by adding the product of the effect size and the dose of each effect allele to the base PRS. This will be referred to as $PRS_{HLA+}$. The $PRS_{HLA+}$ is calculated for all individuals in a validation cohort and obtain metadata (e.g. mean, standard deviation, etc). A RR is calculated using the OR derived from the $PRS_{HLA+}$ model and the prevalence of disease in the validation cohort. This is then used be used to estimate lifetime risk of disease

Figure 11:
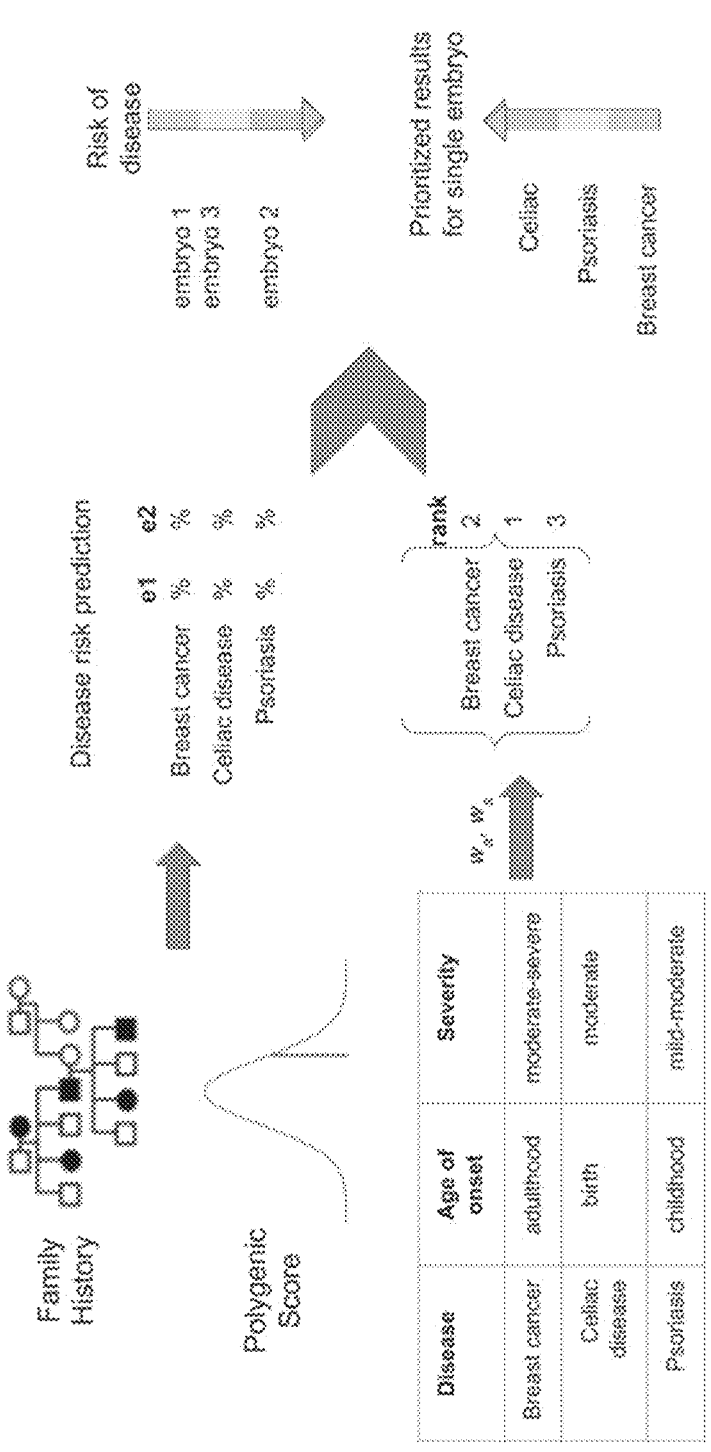
FIG. 11 illustrates an exemplary method of predicting disease risk associated with an embryo.

Example 4: A Method to Rank Disease Risk Profiles with Application to Embryo and Sperm Donor Selection Provided are exemplary methods of ranking disease risk profiles, such as that illustrated in FIG. 11. Initially, a weight, $w_d$, is calculated for each disease in a set of d diseases that is the sum of the weights for age of onset, $w_a$, and disease severity, $w_s$. $w_a$ is greater for diseases with an onset at birth, for example celiac, than for a disease that doesn't generally appear until adulthood, like coronary artery disease. Similarly, $w_s$ is greater for a more severe disease like breast cancer than for a disease with a milder phenotype like vitiligo.

Next, family history and polygenic risk scores are combined to generate a predicted risk for each condition of interest for each embryo.

Finally, the disease ranking and risk prediction are combined to generate a single score, $S_T$, for each embryo using the following equation, where RR is the relative risk derived from the combination of family history and polygenic risk score for a given disease:

$$S_T = \sum_{i=1}^{d} w_d * RR$$

Assume $w_s$=0.5, 1, or 2 for an onset at adulthood, childhood, or birth, respectively. Similarly, assume $w_a$=0.5, 1, or 2 for mild, moderate or severe disease phenotype, respectively, with the ability to choose a mid-value for disease with a variable phenotype. The following Table 4 lists the weights for a small set of conditions based on these values:

TABLE 4

Weights for various conditions

| Disease | Age of onset | $w_a$ | Severity | $w_s$ | $w_d$ |
|---|---|---|---|---|---|
| Breast cancer | adulthood | 0.5 | moderate-severe | 1.5 | 2 |
| Celiac disease | birth | 2 | moderate | 1 | 3 |
| Psoriasis | childhood | 1 | mild-moderate | 0.75 | 1.75 |

Assuming three embryos with the following RR for each of the above conditions, an overall score is calculated for each embryo and ranked accordingly. For embryo 1, the score is calculated as follows:

$$S_T = (2*2.4) + (3*1.4) + (1.75*2.7) = 24.85$$

Disease risk for each of the three embryos is set forth in Table 5.

TABLE 5

Disease risk profiles for three embryos

| Disease | RR Embryo 1 | RR Embryo 2 | RR Embryo 3 |
|---|---|---|---|
| Breast cancer | 2.4 | 1.1 | 0.7 |
| Celiac disease | 1.4 | 1.6 | 1.4 |
| Psoriasis | 2.7 | 7.3 | 2.7 |
| $S_T$ | 13.7 | 19.8 | 10.3 |
| Rank | 2 | 3 | 1 |

The same procedure is applied to sperm donor selection, where each donor receives a ranking across all diseases of interest. In both the embryo and donor selection context, a score is calculated for a subset of diseases (e.g. conditions for which the prospective parents have a family history) or across all diseases for which a polygenic model is implemented.

Alternatively, the method could be used without summing over all conditions of interest to prioritize results for a single embryo/individual. Each condition would receive a score and the condition with the highest score(s) would be prioritized. Using embryo 1 above as an example, the scores and rankings set forth in Table 6 were generated.

TABLE 6

Embryo scores and rankings

| Disease | RR Embryo 1 | Disease Score ($RR*w_d$) | Disease rank |
|---|---|---|---|
| Breast cancer | 2.4 | 4.8 | 1 |
| Celiac disease | 1.4 | 4.2 | 3 |
| Psoriasis | 2.7 | 4.7 | 2 |

Example 5: Prediction of Transmission of Disease Susceptibility Variant to Embryos One copy of a colorectal cancer susceptibility variant (APC c.3920T>A) (and/or insertions, deletions, and/or copy number variants) is found in the father's WGS. The allele is not present in the mother. This variant is not directly measured in the sparse genotyping of the embryos. Whole chromosome haplotypes of parents are obtained from any single or combination of methods described above. Reconstruction of the embryo's genome determines that the haplotype block containing the risk allele is transmitted from the father to one of the embryos. The risk allele is noted as "Present" in the embryo.

Example 6: Polygenic Risk for Common Disease Using Embryo Prediction

Breast cancer has a common genetic component. A genetic risk score uses 69 variants to assess risk of breast cancer. Of these variants, only 13% (9/69) are directly genotyped in the embryo. The percentile of the genetic risk score of the embryo based on these variants is 84.6%. After embryo reconstruction, 98.6% (68/69) of the embryo's genotypes have been imputed/inferred and the new percentile of genetic risk score of the embryo is 77.7%. After the embryo was born, the child's DNA was genotyped and a PRS percentile was 76.2%. This demonstrates that the genetic risk score from a whole genome embryo reconstruction has higher accuracy and less uncertainty due to information on additional variants.

Figure 12:
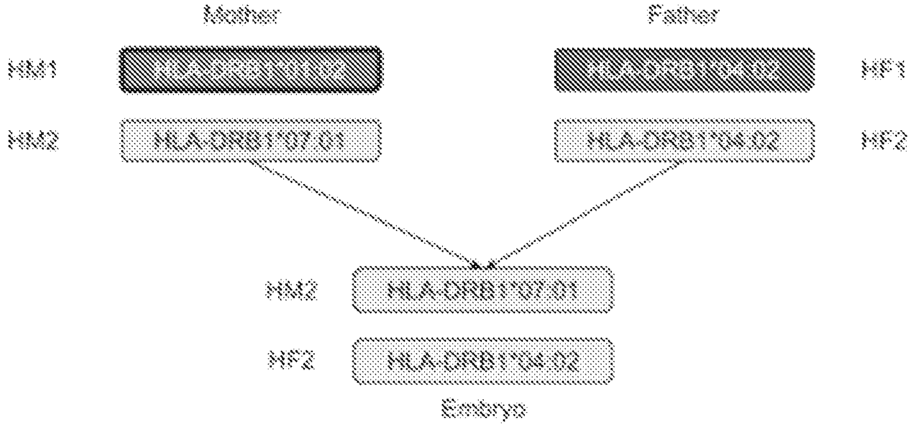
FIG. 12 illustrates an exemplary disease risk transmission prediction chart associated with HLA typing for rheumatoid arthritis.

Example 7: Prediction of Transmission of Disease Associated HLA Types to Embryos A mother is affected by rheumatoid arthritis (RA). HLA typing results (from WGS, PCR+Sanger sequencing or any other appropriate method) reveals that she carries one copy of an HLA-DRB1*01:02 allele associated with increased risk of this condition. The father is homozygous for an HLA-DRB1*04:02, an allele that is not known to be associated with increased risk of RA. Based on full phasing of chromosome 6 in each parent and reconstruction of the embryo genome it is determined that haplotype 2 of the mother (HM2) and haplotype 2 of the father (HF2) are transmitted to the embryo. The RA risk allele is carried on haplotype 1 of the mother (HM1), therefore it is predicted that the embryo does not carry the risk allele. See, e.g., FIG. 12.

Example 8: Providing Families with the Spectrum of Disease Risk in their Children Two parents present to a physician that they are interested in the risk of various genetic diseases in their future children. The methods described above are used to specifically calculate midparent mean and recombination to predict the range of the child's disease risk given two parents' genomes to guide future IVF treatments. See FIG. 9.

Figure 9:
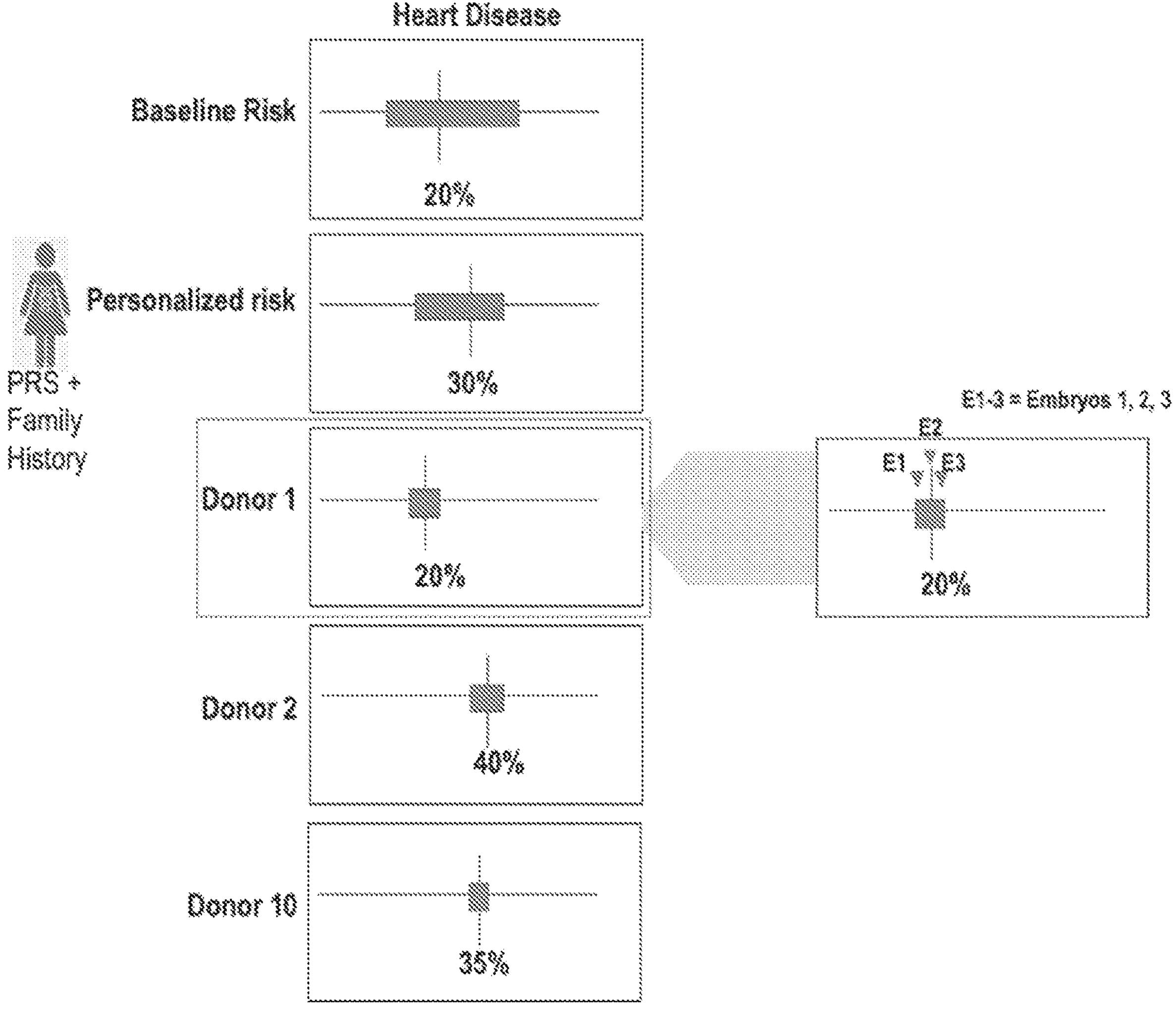
FIG. 9 provides an exemplary disease risk distribution associated with a variety of sperm donors.

Similarly, in the event of sperm donation, a distribution of polygenic risk scores based on WGS of mother and potential sperm donor(s) can be simulated by recombination (see FIG. 9).

Example 9: Incorporation of Family History (FHx) to Improve Risk Estimates

Risk of developing psoriasis is estimated to be 10-30% based on family history of disease. Using a polygenic model alone in embryos where one parent is affected by psoriasis shows only a minor difference in risk across embryos. Incorporating family history provides a much better separation between embryo 1 and embryos 2 and 3 and it is clear that embryos 2 and 3 have additional risk factors beyond FHx, as shown in Table 7.

TABLE 7

Embryo risk scores that incorporate family history

| | Without FHx | | | With FHx | | |
|---|---|---|---|---|---|---|
| | OR | RR | Lifetime risk | OR | RR | Lifetime risk |
| Embryo 1 | 0.99 | 0.99 | 4.0% | 2.76 | 2.69 | 10.7% |
| Embryo 2 | 2.85 | 2.77 | 11.1% | 8.13 | 7.30 | 29.2% |
| Embryo 3 | 3.74 | 3.58 | 14.3% | 10.75 | 9.30 | 37.2% |

Similarly, family history can be incorporated to improve risk estimates in predicting transmission of disease associate HLA types.

Example 10: Incorporation of HLA Typing into Psoriasis Disease Risk Estimates

The presence or absence of two HLA-types associated with risk of developing psoriasis make a clear impact on overall disease risk across embryos. This example can be extended to the context of sperm donor selection or personal genome report, as shown in Table 8.

TABLE 8

Lifetime risk of psoriasis in multiple embryos

| | HLA-C*06:02 | HLA-C*12:03 | $OR_{prs}$ | RR | Lifetime Risk |
|---|---|---|---|---|---|
| Embryo 1 | absent | 1 copy | 0.67 | 0.83 | 3.3% |
| Embryo 2 | 1 copy | 1 copy | 0.75 | 2.91 | 11.6% |
| Embryo 3 | 1 copy | absent | 0.88 | 2.49 | 10.0% |

Family history can be incorporated to further improve risk estimates in predicting transmission of disease associate HLA types. This technology can be extended predict blood type from embryo genome inclusive of Rh status of resulting fetus.

Example 11: Improving Trait Prediction Accuracy

When the genotypes of variants in a polygenic model are unknown in the embryo, parental genotypes can be used to improve trait prediction accuracy. The probability of possible genotypes given the parental genotypes at that site(s) is used instead of a population allele frequency (AF) or an imputed genotype. Using the probabilities in Table 9 below a dose for each possible genotype is added to the risk score. In practice, this improves prediction accuracy as measured by predicted percentile of polygenic risk as shown in Table 10 below which shows improvement in prediction for a polygenic model for Crohn's disease where 4 variants are not predicted in the embryo. The true polygenic risk score percentile ("Truth") is determined using direct genotyping from WGS.

TABLE 9

Embryo genotype probabilities based on parental genotypes

| Mother | Father | P(AA\|M, D) | P(AT\|M, D) | P(TT\|M, D) |
|---|---|---|---|---|
| AT | TT | 0 | 0.25 | 0.75 |

TABLE 10

Percentile of polygenic risk score

| Truth | Population AF | Dosage |
|---|---|---|
| 73.9% | 62.5% | 71.2% |

Example 12: Haplotype Disease Risk

Some disease risks are based on phased haplotypes rather than individual variants. Embryo reconstruction generates phased haplotypes for more accurate prediction of trait risk. Table 11 below lists haplotypes in the gene APOE and their associated risks with Alzheimer's disease (Corder, et al. 1994).

TABLE 11

| Haplotypes in APOE and associated risks with Alzheimer's disease | | | |
|---|---|---|---|
| Haplotype | rs429358 allele | rs7412 allele | Risk for Alzheimer's Disease |
| ε2 | T | T | Protective |
| ε3 | T | C | Neutral |
| ε4 | C | C | Risk |

The two variants are 138 bp apart in the APOE gene. Neither rs429358 or rs7412 are measured among the sparse measurements in the embryo. This precludes estimating Alzheimer's disease risk in the embryo. However, the embryo reconstruction method uses the parents' genotype to predict a fully phased embryo genome that can be used to infer that the embryo is 3/3. This result is later validated by whole-genome sequencing of the born child.

TABLE 12

| Risk for Alzheimer's Disease in reconstructed embryo | | |
|---|---|---|
| | APOE Haplotype | Risk for Alzheimer's Disease |
| Mother | ε3/ε3 | Neutral |
| Father | ε3/ε3 | Neutral |
| Reconstructed Embryo | ε3/ε3 | Neutral |
| Embryo without Reconstruction | Not available | Not available |

Therefore, embryo reconstruction enables APOE haplotypes and Alzheimer's risk prediction and in general, disease status based on haplotypes.

Example 13: Sparse Genotype Scaffold

Figure 13:
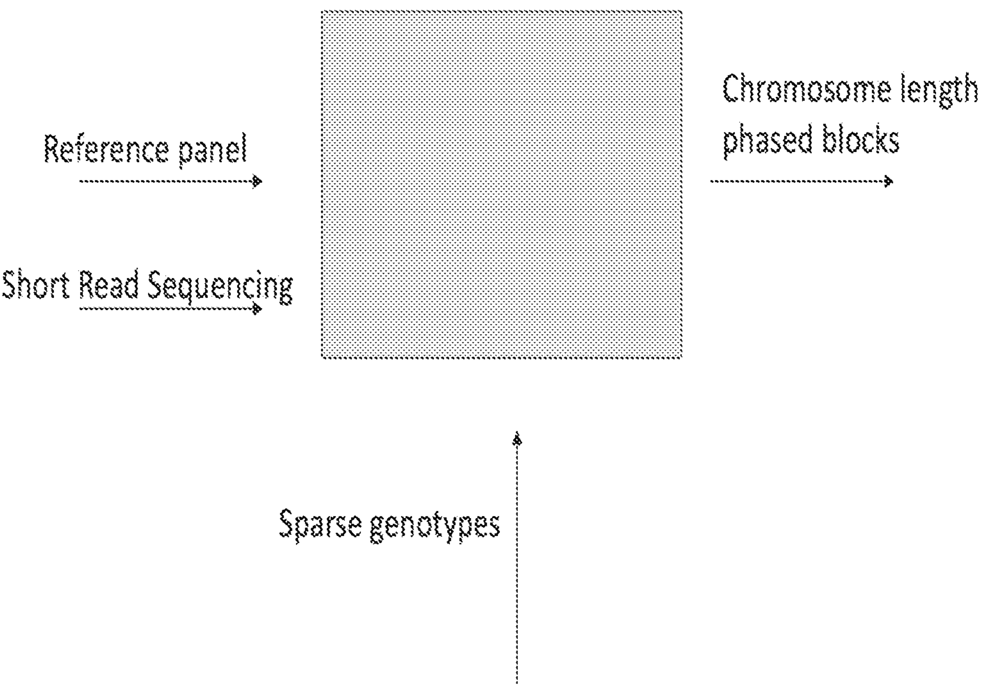
FIG. 13 provides an exemplary scaffold for identifying chromosome length phased blocks for improving disease risk predictive capabilities.

Using sparse genotypes as a scaffold in phasing the entire genome (see, e.g., FIG. 13) improves performance over a reference panel alone as measured by switch error rate (SER). Applying this technique to the well-studied sample NA12878 we saw a drop in overall SER from 0.6% using 1000 Genomes reference panel alone to 0.54% using a set of ~140 k high confidence phased genotypes as a scaffold in combination with the reference panel. This difference is due in large part to a reduction in long switch errors. For example, on chromosome 1, there is a >60% reduction in the raw number of long switch errors (169 vs. 60). Overall, the combined approach (scaffold+reference panel) resulted in a reduction from 0.12% to 0.04% in long switch error rate. This is important in embryo reconstruction as long switch errors will result in incorrect blocks predicted to be transmitted.

Example 14: Polygenic Risk Scores

Large-scale genome-wide association studies (GWAS) have identified genetic variants associated with a wide variety of diseases. These associations have paved the way for functional studies of disease biology, drug target discovery and improved disease risk prediction. While individual common genetic variants may have little predictive value, combining these variants into genetic risk scores can explain a greater proportion of genetic risk for a disease. These multi-locus genetic risk scores, also called polygenic risk scores (PRSs), are most commonly computed as the weighted sum of disease-associated genotypes $$PRS_{ind} = \sum_{i=1}^{n} w_i G_i$$

Where $PRS_{ind}$ is the polygenic risk score for a given individual and disease with n associated variants, $w_i$ is the weight for the ith variant, usually drawn from the GWAS effect size, and $G_i$ is the individual's genotype for the risk allele of the ith variant. PRSs have recently been investigated for their potential to predict risk in a variety of diseases, including cardiovascular disease, breast cancer and type 2 diabetes mellitus. These approaches demonstrated the ability to stratify individuals by their risk for these diseases. Described is a method to validate and implement polygenic models as well as visualize risk estimates in a consumer report.

Choosing a Polygenic Risk Model

Previously published polygenic models for each condition of interest which have been tested on at least 1000 individuals from a broad population were prioritized. This excluded small studies with limited statistical power and studies tested on isolated populations, which may not translate to other populations. Models using data from individuals in the UKBB study set were also excluded. Models that reported an Area Under the Curve (AUC) of greater than 0.65, and/or an odds ratio (OR) greater than 2 for individuals in the top vs. bottom quantile (see below for further information) were chosen. A list of traits with published models and their evaluation statistics is shown in Table 13.

TABLE 13

| Published disease models | | | | |
|---|---|---|---|---|
| Disease | Published Model (PMID) | Size of study cohort | AUC | Quantile or Other Stats |
| Age-related macular degeneration | 21402993 | 1335 cases, 509 controls | 0.82 | |
| Atrial fibrillation | 5123217, 29534064 | 27,471 | N/A | HR = 2.0 for top vs. bottom quintile |
| Breast cancer | 25855707 | 33673 cases, 33381 controls | 0.622 | OR = 3.36 for top 1% compared to middle |

TABLE 13-continued

| Published disease models | | | | |
|---|---|---|---|---|
| Disease | Published Model (PMID) | Size of study cohort | AUC | Quantile or Other Stats |
| Coronary heart disease | 25136350 | 8491 | 0.7-0.78 depending on clinical risk score | RR = 1.28-1.31 per unit change |
| Celiac disease | 24550740 | 5 data sets: 1050-10,304 | 0.87 | |
| Chronic Lymphocytic Leukemia | 29674426 | 1499 cases, 2459 controls | 0.79 | OR = 3.64 (2.94-4.51) for top vs middle quintile |
| Colorectal cancer | 29403313 | 2363 cases, 2198 controls | Not reported | OR = 3.0 for top vs. bottom decile; OR = 1.8 for top 1% vs. middle 40-60% |
| Rheumatoid arthritis | 27912794 | 2785 cases, 1941 controls | Not reported | OR = 4.99 for top vs. bottom quartile |
| Familial hypercholesterolemia | 25414277 | 1158 cases, 3020 controls | 0.673 | |
| Glaucoma | 30972231 | ~435 k (UKBB) | 0.766 | |
| Hyperthyroidism | 30367059 | Up to 21 k | Not reported | OR = 0.19 for top vs. bottom quartile |
| Hypothyroidism | 30367059 | Up to 21 k | Not reported | OR = 2.53 for top vs. bottom quartile |
| Melanoma | 29779563 | 1404 cases, 23798 controls | Not reported | OR = 2.4 for top vs. bottom quartile |
| Multiple sclerosis | 21244703 | 3606 | 0.769 | 79.9% sensitivity and 95.8% specificity in discovery set (n = 8844). 62.3% sensitivity and 75.9% specificity in validation set |
| Psoriasis | 21559375 | 2815 | 0.72 | OR = 10.55 for top vs. bottom quartile |
| VTE | 22586183 | 2712 cases, 4634 controls | 0.69 | OR = 0.37 for individuals with no risk alleles and 7.48 for ≥ 6 risk alleles |
| T1D | 30655379 | 6481 cases, 9247 control | 0.92 | |
| T2D | 19020323 | 2377 | 0.615 | OR = 1.12 per risk allele |
| Prostate cancer | 29779563 | 1425 cases, 9793 controls | Not reported | OR = 3.3 for top vs. bottom quartile |
| Depression | 25343367 | 3091 | Not reported | OR = 1.36 per s.d. For having high CESD score |
| Migraine | 28656458 | 446 cases, 2511 controls | Not reported | OR = 1.56 for top vs. bottom quartile |

When a published model was not available, SNPs were used that met a genome-wide significant p-value threshold (p<5e-8) from the GWAS catalog to construct a score as previously described (PMID: 30309464)

Defining Each Phenotype in the UK Biobank

Data from the UK Biobank cohort was used to validate and standardize each model. This resource includes both genetic and disease information on 500,000 individuals. Only unrelated individuals were used for the analysis below. A combination of ICD-9 and ICD-10 codes, self-reported diseases as well as procedure codes to define each phenotype of interest were used, as shown in Table 14.

TABLE 14

UKBB Phenotype definitions for each trait evaluated

| Disease | ICD9/10 codes (ICD10), (ICD9) | Phenotype terms (UKB data field, description, coding) |
|---|---|---|
| AMD | (H353), (3625) | (6148, Eye problems/disorders, 5), (20002, self-reported, 1528), (5912, Which eye(s) affected by macular degeneration, 1, 2, 3), |
| Asthma | (J45), (493) | (20002, non-cancer self-reported, 1111) |
| Atrial fibrillation | (148), (4273) | (41272, OPCS4, K521, K621, K622, K623) |
| Breast cancer | (C50, D05), (174, 2330) | (20001, self-reported cancer, 1002) |
| Lupus | (M32),(710) | (20002, non-cancer self-reported, 1381) |
| Celiac disease | K900), (5790) | (20002, non-cancer self-reported, 1456) |
| Coronary artery disease | (120,121,122), (410, 411) | (41272, OPCS4, K49, K50, K75, K40, K41, K42, K43, K45, K46), (20002, self-reported, 1075) |
| Chronic lymphocytic leukemia | (C911), (2041) | (20001, self-reported cancer, 1055) |
| Colorectal cancer | (C18), (153) | (20001, self-reported cancer, 1020, 1022) |
| Rheumatoid arthritis | (M05), (7140) | (20002, non-cancer self-reported, 1464) |
| Hyperthyroidism | (E05) | (20002, non-cancer self-reported, coding 1225 (hyperthyroidism) 1522 (grave's disease)) |
| Melanoma | (C43, C44), (172) | (20001, self-reported cancer, 1059) |
| Multiple sclerosis | (G35), (340) | (20002, non-cancer self-reported, 1261) |
| Obesity | | (21001, BMI, >30) |
| Psoriasis | (L40), (696) | (20002, self-reported, 1453) |
| Venous thromboembolism | (182), (453) | (20002, self-reported, 1068) |
| Type 1 diabetes | (E10), (25001, 25011, 25021, 25091) | (20002, self-reported, 1222), all conditioned on (2976, age of diabetes diagnosis, <35) |
| Type 2 diabetes | (E11), (25000, 25010, 25020, 25090, 2503, 2504, 2505, 2506, 2507) | (30750, hba1c, >48), (2443, diabetes diagnosed by doctor, 1), (6177, medications for blood pressure, diabetes, etc, 3), all conditioned on (2976, age of diabetes diagnosis, >35) |
| Glaucoma | (H40), (365) | (20002, non-cancer self-reported, coding 1277) |
| Hypothyroidism | (E02, E03), (244) | (20002, non-cancer self-reported, 1226) |
| Schizophrenia | (F20), (295) | (20002, non-cancer self-reported, 1289), (20544, Mental health problems ever diagnosed by a professional, 2) |
| Prostate cancer | (C61), (185) | (20001, cancer self-reported, 1044) |
| Ovarian cancer | (C56), (183) | (20001, cancer self-reported, 1039) |
| Crohn's disease | (K50) | (20002, non-cancer self-reported, 1462) |
| Ulcerative colitis | (K51) | (20002, non-cancer self-reported, 1463) |
| IBD | (K50, K51) | (20002, non-cancer self-reported, 1462, 1463) |
| Migraine | (G43), (346) | (20002, non-cancer self-reported, 1265) |
| Depression | | (20126, Bipolar and major depression status, 3, 4, 5), (20447, Depression possibly related to stressful or traumatic event, 1), (20123, Single episode of probable major depression, 1), (20124, Probable recurrent major depression (moderate), 1), (20125, Probable recurrent major depression (severe), 1), (20002, non-cancer self-reported, 1286) |
| Bipolar disorder | (F31) | (20002, non-cancer self-reported, 1291) |
| Anxiety | (F33, F34) | (20002, non-cancer self-reported, 1287, 1288) |
| Lung cancer | (C34), (162) | (20001, cancer self-reported, 1001, 1027, 1028) |
| Thyroid cancer | (C73) | (20001, cancer self-reported, 1065) |
| Pancreatic cancer | (C25) | (20001, cancer self-reported, 1026) |
| Non-Hodgkin's lymphoma | (C85, C83) | (20001, cancer self-reported, 1053) |
| Bladder cancer | C(67) | (20001, cancer self-reported, 1035) |

A subset of diseases is shown below in Table 15.

TABLE 15

Frequency of a subset of diseases in the UK Biobank

| Disease | Frequency |
|---|---|
| Celiac Disease | 0.62% |
| Coronary Artery Disease | 6.64% |
| Atrial fibrillation | 4.29% |
| Breast Cancer | 3.66% |

The individuals were stratified by their polygenic risk score (PGS) and the incidence of disease in this population was investigated.

Evaluating a Model Using the UKBB Dataset

Polygenic risk scores were calculated as a weighted sum of disease associated genotypes. Scores for each individual in the UKBB were calculated and a variety of metrics were used to evaluate the performance of a model

PRS Distribution Across Cases and Controls

Figure 14:
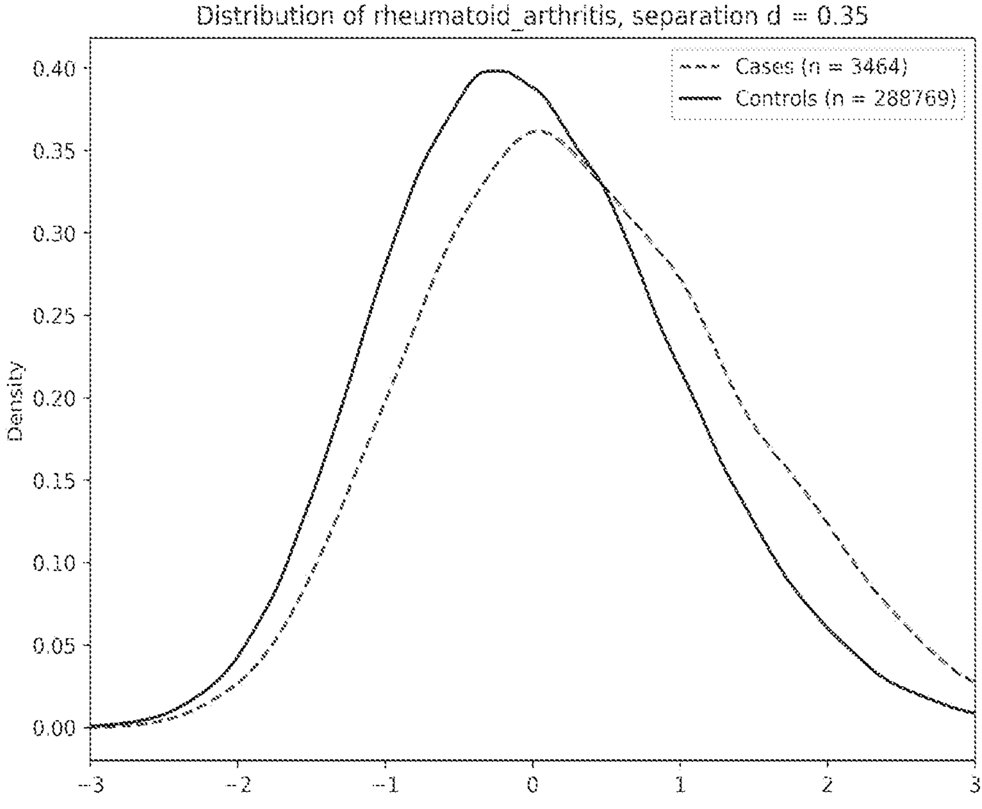
FIG. 14 provides a graphical representation of distributions (mean scaled to 0 and standard deviation of 1) of PRS for rheumatoid arthritis cases and controls

The data set was broken into cases and controls for each trait and the distribution of scores was generated for cases and controls separately. Visual inspection of these distributions gave a general idea of how well each model can distinguish cases from controls. As an example, FIG. 14 shows distributions (mean scaled to 0 and standard deviation of 1) of PRS for rheumatoid arthritis cases and controls.

Receiver Operating Curve (ROC)

The ROC and area under the curve (AUC) were calculated by plotting sensitivity and specificity of the model at different risk thresholds.

Stratification into Deciles of PRS

Figure 15:
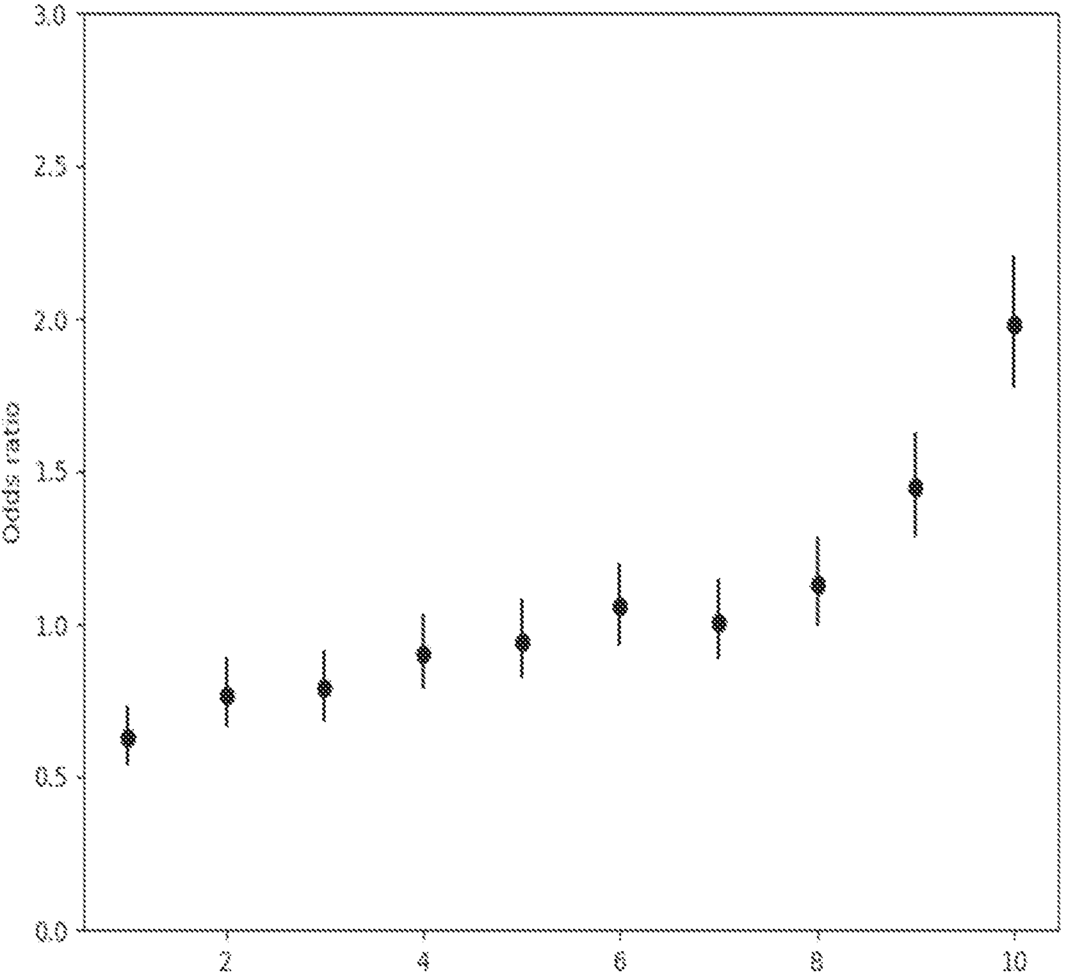
FIG. 15 shows an OR per decile for rheumatoid arthritis.

Individuals in the UK Biobank were stratified into groups with different risk profiles for disease. Individuals in the highest risk (top decile of PRS) were compared with individuals with median-risk (those with PRS in the middle 40-60th percentiles of the distribution). Disease prevalence was plotted for each disease across deciles and the ratio of high risk to median-risk was calculated across diseases. FIG. 15 shows an OR per decile for rheumatoid arthritis.

Regression Analysis Incorporating Age and Sex

After calculating the PRS across all unrelated individuals in the UK biobank dataset, a logistic regression was applied to each model. $\beta_{PGS}$ is the regression coefficient of the PRS and corresponds to the odds ratio when PRS is standardized to a mean of zero and standard deviation of 1. Age and sex were incorporated where available and applicable.

$$LOR|GS = \beta_0 + \beta_{PRS}PRS + \beta_{age}\text{ mean(age)}$$

The odds ratios were then used to determine thresholds for high risk vs. intermediate result for the purpose of the report.

OR SD Per Disease (Mean Centered Vs. z Transformed)

As per the logistic model presented above, the OR/SD of the PRS were obtained by standardizing the PRS variable (mean 0, SD 1) prior to computing the effect size. This process helps achieve two goals. First, the risk stratification ability of PRSs can be directly compared across diseases. PRS for different diseases vary in the number of SNPs and their respective effect sizes, and therefore are on very different scales. Their corresponding effect sizes, if non standardized, will also not be directly comparable. By standardizing all PRSs, models can be directly ranked based on their OR/SD, which results in a ranking reflecting their ability to separate the population based on disease risk. Second, it permits statistically accurate application of UKBB effect estimates to a US population. The UKBB was used to estimate effect sizes, which were then converted into odds ratios. When relative risks were estimated from these odds ratios (see below), the population disease prevalence in the US was used to accurately capture relative risk for an individual with a given PRS in the US. Standardization of the UKBB PRS (using the UKBB mean and SD) allows the PRS of a US individual to be used in the model (after adjustment with the US PRS mean and SD). Due to random assortment in genetics, similar mean and SD of PRSs across populations can be expected, at least for individuals with European ancestry. The results from the analysis are shown in Table 16.

TABLE 16

Model validation statistics

| Phenotype | n_cases | n_controls | AUC | log(OR)/s.d. |
|---|---|---|---|---|
| Age-related macular degeneration (ARMD) | 3913 | 454172 | 0.59 | 0.278 |
| Anxiety | 57740 | 400345 | 0.628 | 0.457 |
| Atrial fibrillation | 20682 | 437403 | 0.652 | 0.381 |
| Bladder carcinoma | 2081 | 456004 | 0.602 | 0.290 |
| Bipolar disorder | 2315 | 455770 | 0.622 | 0.427 |
| Breast cancer | 17438 | 440647 | 0.625 | 0.432 |
| Coronary artery disease | 31528 | 426557 | 0.603 | 0.368 |
| Celiac disease | 3101 | 454984 | 0.827 | 1.031 |
| CLL | 804 | 457281 | 0.707 | 0.667 |
| Colorectal cancer | 5097 | 452988 | 0.603 | 0.294 |
| Crohn's disease | 2446 | 455639 | 0.601 | 0.380 |
| Depression | 95446 | 362639 | 0.623 | 0.321 |
| Glaucoma | 9428 | 448657 | 0.748 | 0.946 |
| Hypothyroidism | 29446 | 428639 | 0.674 | 0.154 |
| Inflammatory bowel disease | 6532 | 451553 | 0.608 | 0.387 |
| Lung carcinoma | 2661 | 455424 | 0.565 | 0.130 |
| Melanoma | 19778 | 438307 | 0.598 | 0.348 |
| Migraine | 17389 | 440696 | 0.637 | 0.150 |
| Multiple sclerosis | 2081 | 456004 | 0.57 | 0.234 |
| Non-Hodgkins lymphoma | 1129 | 456956 | 0.567 | 0.144 |
| Ovarian cancer | 1667 | 456418 | 0.55 | 0.168 |
| Pancreatic carcinoma | 703 | 457382 | 0.609 | 0.365 |
| Prostate cancer | 8897 | 449188 | 0.672 | 0.589 |
| psoriasis | 7518 | 450567 | 0.667 | 0.539 |
| Rheumatoid arthritis | 5612 | 452473 | 0.595 | 0.345 |
| schizophrenia | 940 | 457145 | 0.692 | 0.623 |
| Lupus | 746 | 457339 | 0.730 | 0.506 |
| Type 1 Diabetes | 1195 | 456890 | 0.795 | 1.507 |
| Type 2 Diabetes | 19976 | 438109 | 0.641 | 0.491 |
| Thyroid carcinoma | 364 | 457721 | 0.638 | 0.508 |
| Ulcerative colitis | 4686 | 453399 | 0.621 | 0.444 |
| Vitiligo | 260 | 457825 | 0.727 | 0.861 |

PRS Stratification of Disease Vs. Age

After stratifying individuals into different risk groups, the UKBB data was used to estimate the percentage of the population diagnosed with the disease within these different groups. This information was plotted visually across different strata including the high risk (top 5% of individuals by PRS) and average risk (across the population) groups. The predicted percentage diagnosed for a group of individuals at similar genetic risk to our given individual of interest was shown, with the assumption that the individual of interest had a PRS at the 75th percentile.

The plots help illustrate the utility of PRSs in stratifying individuals based on risk for disease. Seeing a clear separation in the proportion of population diagnosed within different PRS strata confirms the ability of the model to separate individuals based on their risk.

Computing an Adjusted Lifetime Risk for an Individual

One can start with the average lifetime risk for their sex for people in the United States. Next, the risk markers in the genome are evaluated and a polygenic score is calculated based on the markers. This information is converted into an "odds ratio" using data from the UKBB described above. Finally, a formula is used to factor this odds ratio and the average lifetime risk to estimate the lifetime risk for an individual with this change:

$$RR = \frac{OR}{1 - p_0 + p_0 * OR}$$

$$\text{adjusted lifetime risk} = c_0 * RR$$

Where $p_0$ is the prevalence of a condition in the UKBB, $c_0$ is the average lifetime risk for a condition in the United State and OR is the odds ratio calculated above. The result is an estimate of the individual's own lifetime risk compared with the population average. For some conditions, average lifetime risk is not available. In these cases, it is indicated whether the genetics analyzed indicate increased risk.

Defining a Threshold of "High Risk"

In some cases, a threshold for high genetic risk was set based on known risk factors. For example, the relative risk of developing Type 1 Diabetes for an individual with an affected first degree relative is 6.6. Therefore, the high risk threshold to the PRS for Type 1 Diabetes was set that corresponded to that relative risk. For phenotypes where this was not available or when the threshold was not achievable with the model, we designated individuals with either a 2× increase in relative risk or a 10% increase in absolute risk as high risk. Evaluation metrics for a subset of phenotypes where lifestyle or clinical factors informed the high risk threshold are shown in Table 17.

TABLE 17

Evaluation of models in a subset of unrelated UKBB individuals

| Disease | Risk Factor (RR) | PPV | NPV | % high risk (%) |
|---|---|---|---|---|
| Rheumatoid arthritis | Smoking (1.9) | 2.9% | 98.9% | 3.5% |
| Coronary heart disease | Family history (1.4) | 9.8% | 93.4% | 3.7% |
| Type 1 Diabetes | Family history (6.6) | 1.9% | 99.8% | XX (4.9%) |

Example 15: Multifactorial Conditions (Polygenic Risk Score)

Genomic DNA obtained from submitted samples was sequenced using either Illumina or BGI technology. Reads were aligned to a reference sequence (hg19) and sequence changes were identified. For some genes, only specific changes were analyzed. Deletions and duplications were not examined unless otherwise indicated above. In some scenarios, independent validation of HLA type may have been performed by an external lab. Selected variants were annotated and interpreted according to ACMG (American College of Medical Genetics) guidelines. Only pathogenic or likely pathogenic variants are reported. Embryo and parent genotyping with subsequent "Parental Support" analysis was performed. Embryo genomes were reconstructed using embryo genotypes and parental whole genome sequences using a Genome Reconstruction algorithm. Only variants observed in the parents' genomes that are predicted to have an impact on the embryo were examined in the reconstructed embryo genomes. For a subset of conditions, a polygenic risk score was calculated. Models for each condition were evaluated on the UK Biobank population. Some polygenic risk scores may be refined using HLA type. An individual's lifetime risk was calculated by adjusting the baseline risk (in the US population) according to their demographic information and polygenic risk score. Models for which the top to bottom decile resulted in a difference of 10% lifetime risk or 1.9-fold increase in lifetime risk were included in the report. Certain conditions (e.g. bipolar disease) were kept in the experimental section as per investigator discretion based on available evidence of model and genome reconstruction performance. The lifetime risk of various conditions for particular embryos is set forth in FIGS. 16A-C.

Figure 17B:
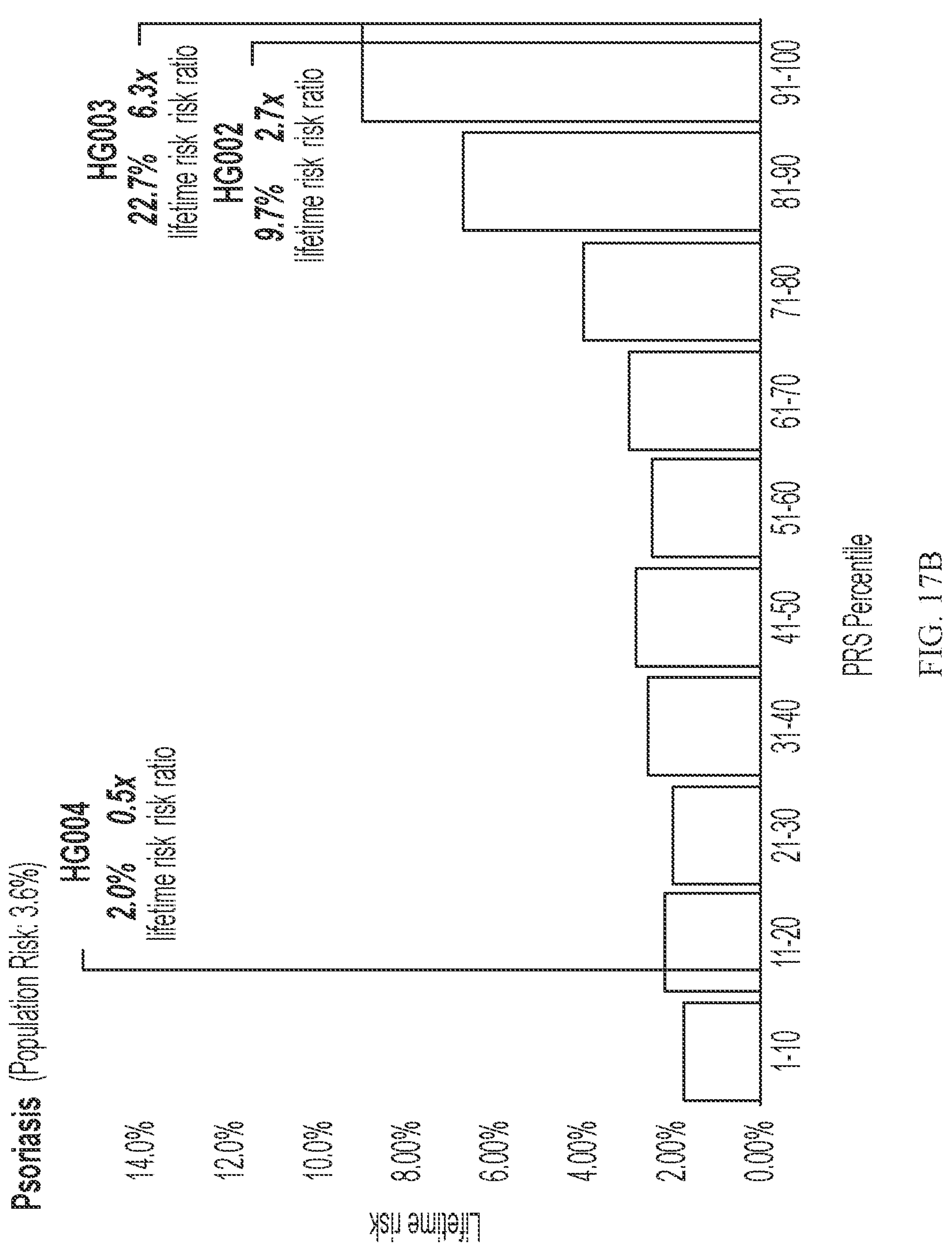
FIG. 17B shows the lifetime risk of the embryos as a function of polygenic risk score.

Using psoriasis as a particular example, FIGS. 17A-B show the risk scores related to a predisposition for psoriasis in three exemplary embryos.

Example 16: Whole Genome Prediction of Embryos Using Haplotype Resolved Genome Sequence Haplotype-resolved genome sequencing were combined with a sparse set of genotypes from single or few-cell embryo biopsies from embryos to predict the whole genome sequence of an embryo. Specifically, stLFR technology was used for haplotype resolved genome sequencing of the father. Performance was evaluated at rare heterozygous positions (defined as allele frequency of 1% or lower). Inheritance of 230,117 sites were predicted in the embryo at 89.5% accuracy.

Materials used in this study were retrospectively obtained from participants who previously underwent a successful round of IVF with preimplantation genetic diagnosis (Table 16). Trophectoderm biopsies from a total of ten embryos (day 5) were genotyped each across a panel of 300,000 common SNPs using an expedited, 24-hour microarray protocol. Additionally, each parent and all four grandparents were genotyped across the same panel.

TABLE 16

Tissue samples used as proof of concept

| Individual | Sample | Type of Sequencing | Purpose | Platform |
|---|---|---|---|---|
| Mother and Father | Blood | WGS | Identify variants | Illumina HiSeq |
| | | Dilution pool | Phase variants into haplotype blocks | 278 pools MDA followed by HiSeq |
| | | Array | Assist in embryo phasing | Illumina CytoSNP |
| Single cell biopsy from embryo(s) | Single cell | Array | 1. Infer parent phase from multiple embryos 2. Estimate haplotype transmission in | Illumina CytoSNP |
| Newborn | Saliva | WGS | Validation | Illumina HiSeq |
| Grandparents | Saliva | WGS | Additional phasing | Illumina HiSeq |
| | | Array | Assist in embryo phasing | Illumina CytoSNP |

Figure 18:
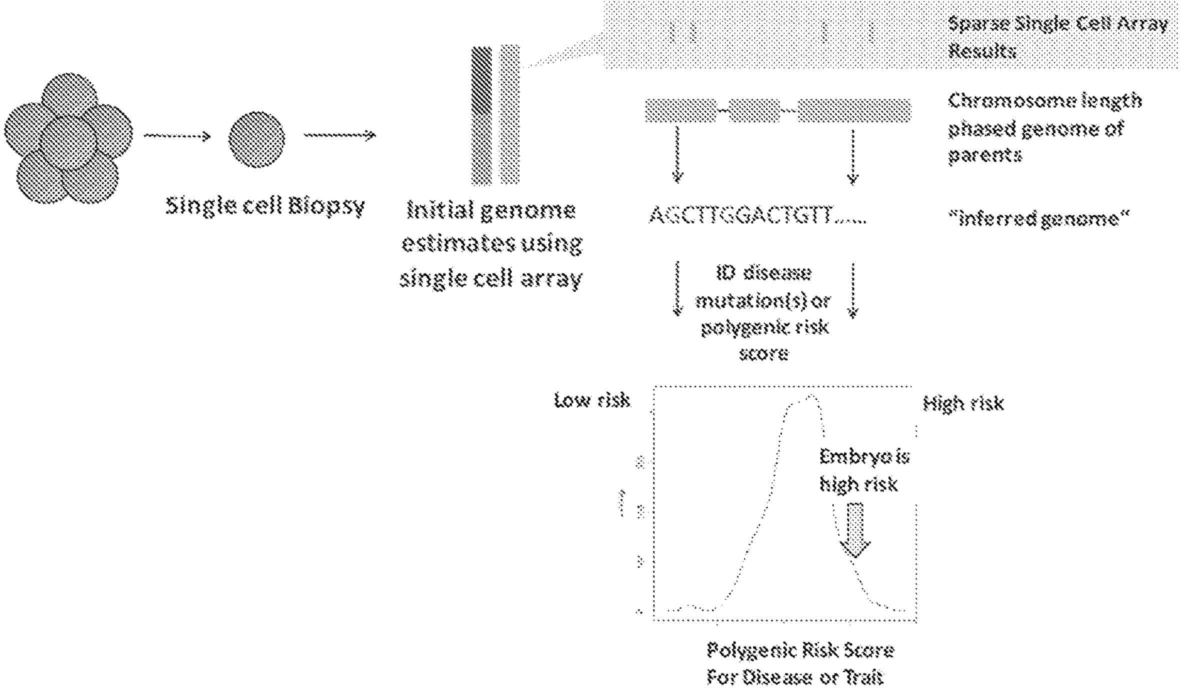
FIG. 18 provides an illustration of an exemplary parental support method for determining embryo disease risk.

Genomic DNA was extracted from whole blood or saliva samples. Newborn and maternal DNA were processed using 30X WGS on BGI platform. Paternal sample was processed using stLFR. Trophectoderm biopsies from one ten day-5 embryos were subjected to DNA extraction, amplification and genotyping with parents and grandparents using a rapid microarray protocol with the Illumina CytoSNP-12 chip used across all samples. Sibling embryo and parent SNP array measurements were combined using a "Parental Support" (PS) method (FIG. 18, 19) as detailed in Kumar et al 2015. The whole genome sequence of the embryo was predicted by combining PS embryo genotypes with parental haplotype blocks (see FIG. 18).

Example 17: Construction of Whole Chromosome Haplotypes from Haplotype Blocks and Parental Information To construct chromosome length haplotypes in an IVF setting, haplotype resolved genome sequencing of both parents was combined with information from sparse genotypes from sibling embryos. As part of the "Parental Support" (PS) method, Maximum Likelihood Estimate (MLE) phase of heterozygous SNVs in each parent are created by combining recombination frequencies from the HapMap database with SNP array measurements from parents and SNP array measurements from sibling embryos. This sparse, chromosome length haplotype was not sufficient to predict the genome of an embryo, but can be combined with molecularly obtained dense haplotypes (e.g. using long fragment read technology, 10× Genomics, CPT-seq, Pacific Biosciences, Hi-C) from parental samples to predict the inherited genome sequence.

The information was obtained using several data streams. To generate dense haplotype blocks, first shotgun sequencing was performed of the mother and father to 34× and 30× median fold coverage, respectively. Next, by sequencing haploid subsets of genomic DNA obtained via in vitro dilution pool amplification, 94.2% of 1.94 million heterozygous SNVs in the mother and 92.4% of 1.89 million heterozygous SNVs in the father were directly phased into long haplotype blocks. These molecularly obtained "dense haplotype blocks" were combined with the sparse, but chromosome length haplotypes to construct chromosome length haplotype resolved genome sequences of the parents. This sequence information was subsequently used to predict the inherited genome sequence of an embryo, but could also be used to predict potential progeny of the two parents (e.g. by simulating potential eggs and sperm that would result in future children).

Figure 19:
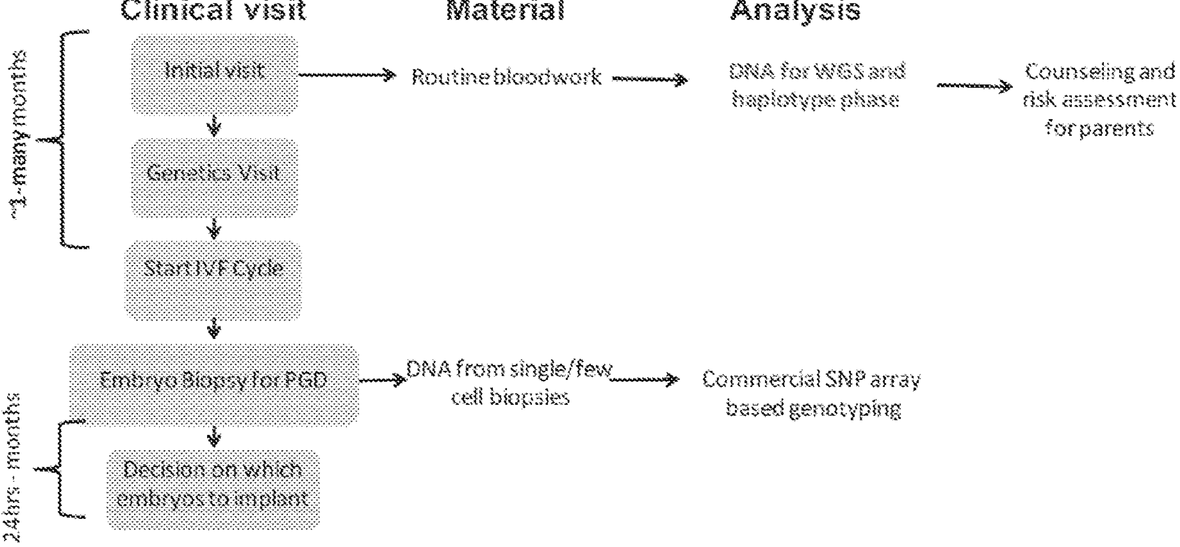
FIG. 19 illustrates a potential workflow for whole genome prediction of embryos.

Potential workflow for whole genome prediction of embryos is shown in FIG. 19. At the initial visit patients give blood which is used for generating whole genome sequence of each parent and is used to predict the possible disorders that the couple is at risk for. After counseling, the parents undergo IVF and the embryos are genotyped using conventional IVF PGD technology and this information is combined with whole genome sequence information of the parents (haplotype-resolved) to predict the inherited genome of the embryo and assess disease risk.

Sibling embryos and parental genotypes are used to construct chromosome-length parental haplotypes. Statistical approaches (e.g. maximum likelihood estimation) are used to determine parental phase from noisy information obtained from each sibling embryo and databases of meiotic recombination frequencies.

Whole Chromosome Haplotype Construction

Figure 20:
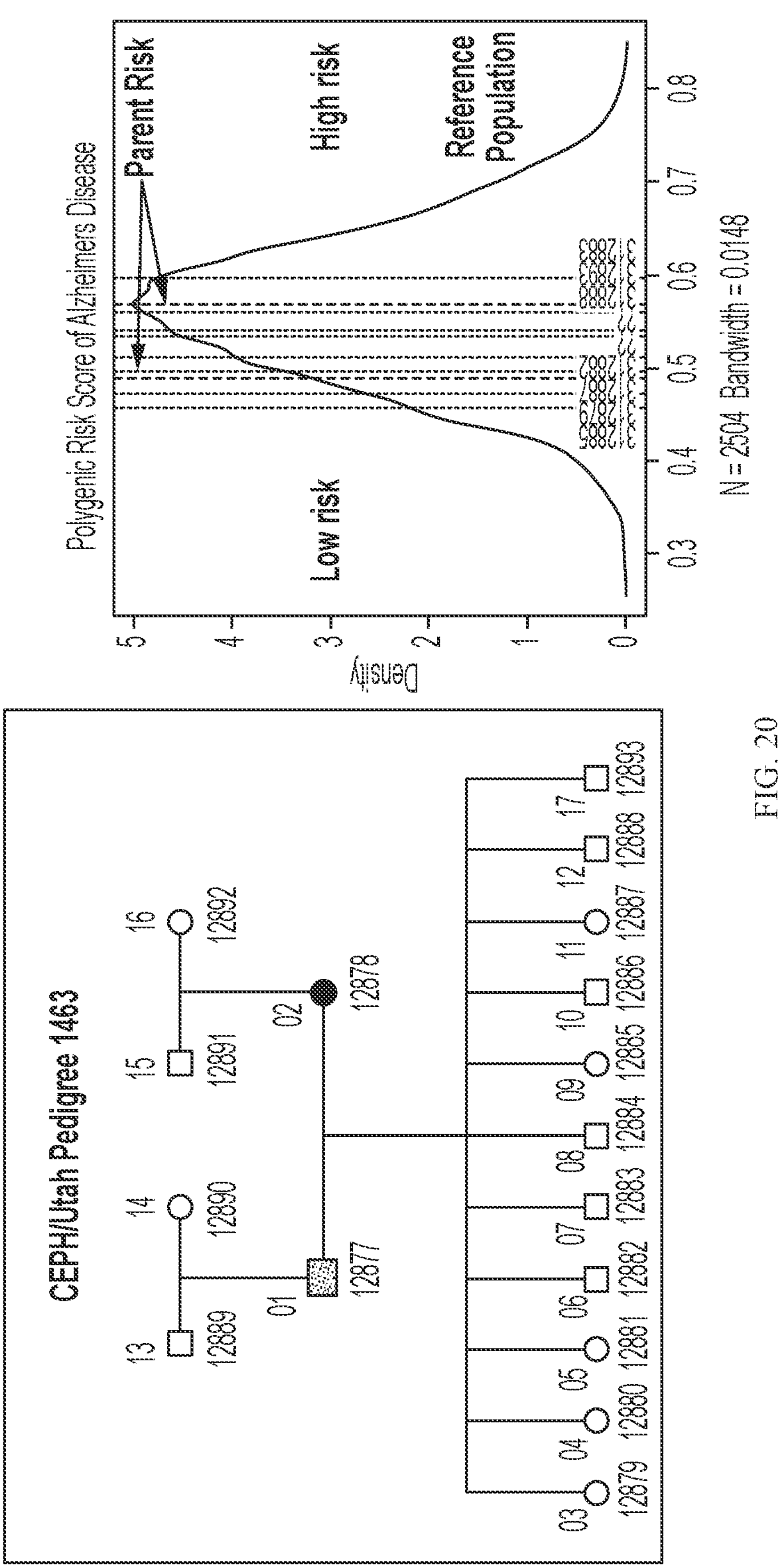
FIG. 20 provides an illustration of how a whole chromosome phase can be obtained of an individual by performing whole genome sequencing of the individual, their partner and two or more children and determining which loci were inherited by each child.

Whole chromosome haplotype are constructed by sequencing the genomes of relatives of an individual, including but not limited to parents, grandparents or children. If an individual has two or more children with the same person, whole chromosome phase can be obtained of the individual by performing whole genome sequencing of the individual, their partner and two or more children and determining which loci were inherited by each child (FIG. 20). This would provide whole chromosome-based haplotype information without a modification to the DNA sequencing process. This would be relevant, for example in the instance where a couple already has two children and is looking to have another and would work in the absence of any grandparental DNA samples.

Chromosome Haplotypes from Individual Sperm

The method of Example 17 is conducted with whole chromosome haplotypes obtained by sequencing DNA obtained from individual sperm.

Example 18: Using Embryo Genome Prediction to Calculate a Polygenic Risk Score for a Genetically Complex Disease Genome wide association studies have enabled the construction of polygenic risk score models for conditions such as Type 1 Diabetes, Schizophrenia, Crohn's Disease, Celiac Disease, Alzheimer's disease etc. These approaches involve taking a list of genome-wide significant SNPs with the observed odds ratio for a SNP to be associated with a disease and calculating a "risk score" for each individual depending on the constellation of SNPs seen in that individual. This approach was used to calculate the polygenic risk score for siblings to simulate the polygenic risk score seen in comparing sibling embryos in an IVF cycle. Genome sequences from a publically available pedigree with 12 siblings, two parents and four grandparents were used. Each genome variant file (VCF file) was converted into a PLINK file and the plink—score command was used on a table of variants to calculate a polygenic risk score for each individual in the family. A polygenic risk score was calculated for each of the siblings as well as the two parents. Polygenic risk scores were also calculated for each individual in the 1000 Genomes cohort (~2500 individuals) as well as a subset of individuals who are Caucasian (~200-300 individuals). The polygenic risk score for each member of the family was compared their polygenic risk score with that of a population matched (European) group of individuals to determine whether the individual was high risk or low risk.

A polygenic risk score for Celiac Disease has been developed within a Caucasian population that incorporates multiple SNPs (Abraham et al 2014; PMC PMC3923679). The model has high sensitivity for Celiac Disease, and one can calculate a negative predictive value of the approach at a certain PRS threshold. We estimate a negative predictive value of 99.4% at a specific PRS (less than −1), assuming a family history of Celiac Disease. After calculating a PRS for each individual, two individuals had a PRS less than this threshold. In an IVF context, we estimate that these two embryos could be chosen for implantation with a decrease in disease risk by approximately 10-fold.

A polygenic risk score for Alzheimer's disease had previously been developed and found to be associated with earlier onset of Alzheimer's (Desikan et. al 2017; PMC5360219; Table 2). Parental PRS are shown in the dark blue dashed lines. Each of the embryo PRS is shown with a gray dashed line. After calculating a PRS for each individual, the individual with the lowest polygenic risk score is predicted to have a reduced risk of Alzheimers disease (median age of onset 87 years instead of 80 years) when compared to the embryo with the highest polygenic risk score.

TABLE 17

Single nucleotide polymorphisms used to construct polygenic risk score for Alzheimer's disease

| SNP | Gene | β (log Hazard Ratio) |
|---|---|---|
| ε2 allele | APOE | −0.47 |
| ε4 allele | APOE | 1.03 |
| rs4266886 | CR1 | −0.09 |
| rs61822977 | CR1 | −0.08 |
| rs6733839 | BIN1 | −0.15 |
| rs10202748 | INPP5D | −0.06 |
| rs115124923 | HLA-DRB5 | 0.17 |
| rs115675626 | HLA-DQB1 | −0.11 |
| rs1109581 | GPR115 | −0.07 |

TABLE 17-continued

Single nucleotide polymorphisms used to construct polygenic risk score for Alzheimer's disease

| SNP | Gene | β (log Hazard Ratio) |
|---|---|---|
| rs17265593 | BC043356 | −0.23 |
| rs2597283 | BC043356 | 0.28 |
| rs1476679 | ZCWPW1 | 0.11 |
| rs78571833 | AL833583 | 0.14 |
| rs12679874 | PTK2B | −0.09 |
| rs2741342 | CHRNA2 | 0.09 |
| rs7831810 | CLU | 0.09 |
| rs1532277 | CLU | 0.21 |
| rs9331888 | CLU | 0.16 |
| rs7920721 | CR595071 | −0.07 |
| rs3740688 | SPI1 | 0.07 |
| rs7116190 | MS4A6A | 0.08 |
| rs526904 | PICALM | −0.20 |
| rs543293 | PICALM | 0.3 |
| rs11218343 | SORL1 | 0.18 |
| rs6572869 | FERMT2 | −0.11 |
| rs12590273 | SLC24A4 | 0.1 |
| rs7145100 | abParts | 0.08 |
| rs74615166 | TRIP4 | −0.23 |
| rs2526378 | BZRAP1 | 0.09 |
| rs117481827 | C19orf6 | −0.09 |
| rs7408475 | ABCA7 | 0.18 |
| rs3752246 | ABCA7 | −0.25 |
| rs7274581 | CASS4 | 0.1 |

Example 19: Relatedness Calculation

Using embryo genotype to calculate a relatedness index with individual with undesirable genetic traits. For example, consider a maternal grandparent with schizophrenia. Step 1: calculate relatedness between each embryo and the affected individual's genome after inferring embryo genome from Example 1 and 2. Step 2: select for embryo with the lowest relatedness with affected individual Example 20: Predict Disease Risk Using Calculated Genetic Relatedness Via Identity by Descent An extension of Example 3 where Identity By Descent (IBD) is used in place of genetic relatedness to an affected individual in disease prediction. As various sibling embryos would have different IBD with an affected familial relative, this information can be used in addition to the PRS score to further refine probability of disease risk of an embryo. The example below assumes that risk for disease is spread equally throughout the genome of an affected individual, and thus risk is linear to the degree of IBD with affected individual.

$$\log(P/(1-P))=\text{beta\_1}*PRS+\text{beta\_2}*\text{sex\_male}+\text{beta\_3}*\text{has\_family\_history}+\text{beta 4}*IBD\text{\_affected\_individual}.$$

Example 21: Regions of Shared Genomic Information

Identifying regions of shared genetic information between two individuals and selecting for embryos that do not contain regions of homozygosity which can increase the chances of a mendelian condition. In consanguineous couples or couples with shared genetic backgrounds, it is possible that progeny will be homozygous for disease causing regions. As genes with known disease association are spread heterogeneously throughout the genome, disease can be minimized by avoiding regions of homozygosity within known disease causing regions of the genome. Step 1: Determine regions of shared genetic information between two parents Step 2: Calculate fraction of homozygous regions in each embryo Step 3: Select for embryos with lowest regions of homozygosity in total or across regions that are known to be disease causing.

What is claimed is:

1. A method for determining a disease risk associated with an embryo, the method comprising:

(a) performing whole genome sequencing on a biological sample obtained from a paternal subject to identify a genome associated with the paternal subject;

(b) performing whole genome sequencing on a biological sample obtained from a maternal subject to identify a genome associated with the maternal subject;

(c) phasing the genome associated with the paternal subject to identify a paternal haplotype;

(d) phasing the genome associated with the maternal subject to identify a maternal haplotype;

(e) performing sparse genotyping on the embryo to identify one or more genetic variants in the embryo;

(f) constructing the genome of the embryo based on (i) the one or more genetic variants in the embryo, (ii) the paternal haplotype, (iii) the maternal haplotype, (iv) a transmission probability of the paternal haplotype, and (v) a transmission probability of the maternal haplotype;

(g) assigning a polygenic risk score to the embryo based on the constructed genome of the embryo;

(h) determining the disease risk associated with the embryo based on the polygenic risk score;

(i) determining transmission of monogenic disease causing genetic variants and/or haplotypes from the paternal genome and/or maternal genome to the embryo; and (j) determining a combined disease risk associated with the embryo based on the polygenic disease risk and the transmission of monogenic disease causing genetic variants and/or haplotypes from the paternal genome and/or maternal genome to the embryo.

2. The method of claim 1, further comprising outputting a combined disease risk associated with the embryo based on the polygenic disease risk and the transmission of monogenic disease causing genetic variants and/or haplotypes from the paternal genome and/or maternal genome to the embryo.

3. The method of claim 1, wherein the method further comprises using grandpaternal genomic data and/or grandmaternal genomic data to determine paternal haplotypes and/or maternal haplotypes.

4. The method of claim 1, wherein the method further uses population genotype data and/or population allele frequencies to determine the disease risk of the embryo.

5. The method of claim 4, wherein the phasing is performed using population-based and/or molecular based methods (e.g. linked reads); and/or wherein the population genotype data comprises allele frequencies and individual genotypes for at least about 300,000 unrelated individuals in the UK Biobank; and/or population phenotype data comprises both self-reported and clinically reported (e.g., ICD-10 codes) phenotypes for at least about 300,000 unrelated individuals in the UK Biobank; and/or the population genotype data comprises population family history data that comprises self-reported data for at least about 300,000 unrelated individuals in the UK Biobank.

6. The method of claim 4, wherein the disease risk is further determined by a fraction of genetic information shared by an affected individual.

7. The method of claim 1, wherein the method further uses family history of disease and/or other risk factors to predict disease risk.

8. The method of claim 1, wherein the whole genome sequencing is performed using standard, PCR-free, linked read (e.g., synthetic long read), or long read protocols.

9. The method of claim 1, wherein the sparse genotyping is performed using microarray technology; next generation sequencing technology of an embryo biopsy; or cell culture medium sequencing.

10. The method of claim 1, wherein the polygenic risk score is determined by summing an effect across sites in a disease model.

11. A method for determining disease risk for one or more potential children, the method comprising:

(a) performing whole genome sequencing on (i) a prospective mother and one or more potential sperm donor(s) or (ii) a prospective father and one or more potential egg donors;

(b) phasing the genomes of (i) the prospective mother and the one or more potential sperm donor(s) or (ii) the prospective father and the one or more potential egg donors;

(c) simulating gametes based on recombination rate estimates;

(d) combining the simulated gametes to produce genomes for the one or more potential children;

(e) assigning at least one polygenic risk score to each of the one or more potential children; and (f) determining a distribution of disease probabilities based on the at least one polygenic risk score.

12. The method of claim 11, wherein the method uses a dense genotyping array for the sperm donor(s) followed by genotype imputation for sites of interest not directly genotyped.

13. The method of claim 11, wherein the method further uses family history of disease and other relevant risk factors to determine disease risk.

14. The method of claim 11, wherein the whole genome sequencing is performed using standard, PCR-free, linked read (i.e. synthetic long read), or long read protocols.

15. The method of claim 11, wherein the phasing is performed using population-based and/or molecular based methods (e.g. linked reads); and/or wherein the population-based methods comprise population genotype data comprising allele frequencies and individual genotypes for at least about 300,000 unrelated individuals in the UK Biobank; and/or population phenotype data comprises both self-reported and clinically reported (e.g., ICD-10 codes) phenotypes for at least about 300,000 unrelated individuals in the UK Biobank; and/or the population family history comprises self-reported data for at least about 300,000 unrelated individuals in the UK Biobank and information derived from relatives of those individuals in the UK Biobank.

16. The method of claim 11, wherein the at least one polygenic risk score is determined by summing an effect across all sites in a disease model.

17. A method for determining a range of disease risk for potential children for (i) a prospective mother and one or more potential sperm donor(s) or (ii) a prospective father and one or more potential egg donor(s), the method comprising:

(a) performing whole genome sequencing on (i) the prospective mother and the one or more potential sperm donor(s) to obtain a maternal genotype and one or more sperm donor genotype(s) or (ii) the prospective father and the one or more potential egg donor(s) to obtain a paternal genotype and one or more egg donor genotype(s);

(b) estimating possible genotypes for one or more potential children using (i) the maternal genotype and the potential sperm donor genotype(s) or (ii) the prospective father genotype and the potential egg donor genotype(s);

(c) phasing (i) the maternal genotype to identify a maternal haplotype or (ii) the paternal genotype to identify a paternal haplotype;

(d) phasing (i) the one or more sperm donor(s) genotype to identify a sperm donor haplotype or (ii) the one or more egg donor genotype(s) to identify an egg donor haplotype;

(e) performing sparse genotyping on the one or more potential children to identify one or more genetic variants in the one or more potential children;

(f) constructing the genome of the one or more potential children based on (i) the one or more genetic variants in the one or more potential children, (ii) the maternal haplotype or the paternal haplotype, (iii) the sperm donor haplotype or the egg donor haplotype, (iv) a transmission probability of the maternal haplotype or the paternal haplotype, and (v) a transmission probability of the sperm donor haplotype or the egg donor haplotype;

(g) estimating a lowest possible polygenic risk score of a potential child using the constructed genome of the one or more potential children; and (h) estimating a highest possible polygenic risk score of a potential child using the constructed genome of the one or more potential children.

* * * * *